United States Patent
Volfman et al.

(10) Patent No.: US 7,483,126 B2
(45) Date of Patent: Jan. 27, 2009

(54) PERFORMANCE ANALYSES OF MICROMIRROR DEVICES

(75) Inventors: Igor Volfman, Sunnyvale, CA (US); Andrew Huibers, Palo Alto, CA (US); Satyadev Patel, Sunnyvale, CA (US); Peter Richards, San Francisco, CA (US); Leonid Frenkel, Palo Alto, CA (US); Jim Dunphy, San Jose, CA (US); Regis Grasser, Mountain View, CA (US); Greg Schaadt, Santa Clara, CA (US)

(73) Assignee: Texas Instruments Incorporated, Dallas, TX (US)

( * ) Notice: Subject to any disclaimer, the term of this patent is extended or adjusted under 35 U.S.C. 154(b) by 457 days.

(21) Appl. No.: 10/875,760

(22) Filed: Jun. 23, 2004

(65) Prior Publication Data
US 2005/0286045 A1    Dec. 29, 2005

(51) Int. Cl.
*G01N 21/88* (2006.01)
*G02B 26/00* (2006.01)

(52) U.S. Cl. .............. 356/218; 356/124; 356/128; 359/190; 359/191

(58) Field of Classification Search ........... 356/72–73, 356/121–122, 124, 128; 250/492.2, 492.3, 250/339.07, 234; 359/290–295, 224, 237
See application file for complete search history.

(56) References Cited

U.S. PATENT DOCUMENTS

| | | | | |
|---|---|---|---|---|
| 5,612,736 A | * | 3/1997 | Vogeley et al. | 348/207.99 |
| 5,796,508 A | * | 8/1998 | Suzuki | 359/224 |
| 5,923,036 A | * | 7/1999 | Tague et al. | 250/339.07 |
| 6,060,224 A | * | 5/2000 | Sweatt et al. | 430/395 |
| 6,088,474 A | | 7/2000 | Dudasko et al. | |

(Continued)

OTHER PUBLICATIONS

Chu, Henry et al., "DMD Superstructure Characterizations", TI Technical Journal, Jul.-Sep. 1998, pp. 75-86.

(Continued)

*Primary Examiner*—Sang Nguyen
(74) *Attorney, Agent, or Firm*—Wade James Brady, III; Frederick J. Telecky, Jr.

(57) ABSTRACT

The invention provides a method and apparatus for evaluating the product quality and performances of micromirror array devices through measurements of the electromechanical responses of the individual micromirrors to the driving forces of electric fields. The electromechanical responses of the micromirrors according to the present invention are described in terms of the rotational angles associated with the operational states, such as the ON and OFF state angles of the ON and OFF state when the micromirror array device is operated in the binary-state mode, and the response speed (i.e. the time interval required for a micromirror device to transit form one state to another) of the individual micromirrors to the driving fields.

11 Claims, 12 Drawing Sheets

U.S. PATENT DOCUMENTS

| | | | |
|---|---|---|---|
| 6,515,278 B2 * | 2/2003 | Wine et al. | 250/234 |
| 6,722,767 B2 * | 4/2004 | Dick et al. | 351/211 |
| 6,788,416 B2 * | 9/2004 | Reuter | 356/445 |
| 6,975,444 B2 * | 12/2005 | Huibers | 359/291 |
| 7,154,660 B2 * | 12/2006 | Reuter | 359/291 |
| 7,345,806 B2 * | 3/2008 | Simonian et al. | 359/291 |
| 2003/0223084 A1 | 12/2003 | Mehri et al. | |
| 2004/0042000 A1 | 3/2004 | Mehri et al. | |

OTHER PUBLICATIONS

Sharpe, Jr., W.N. et al., "Tensile Testing of MEMS Materials—Recent Progress", Journal of Materials Science, 38, 2003, pp. 4075-4079.

Buchheit, T.E. et al., "Micromechanical Testing of MEMS Materials", Journal of Materials Science, 38, 2003, pp. 4081-4086.

Allameh, S.M., "An Introduction to Mechanical-Properties-Related Issues in MEMS Structures", Journal of Materials Science, 38, 2003, pp. 4115-4123.

Allameh, S.M., "Surface Topography Evolution and Fatigue Fracture of Polysilicon", Journal of Materials Science, 38 2003, pp. 4145-4155.

Gall, Ken et al., "Thermomechanical Response of Bare and Al2O3-Nanocoated Au/Si Bilayer Beams for Microelectromechanical Systems", J. Mater. Res., vol. 18, No. 7, Jul. 2003, pp. 1575-1587.

* cited by examiner

178

Polarity
○ Positive  ○ Negative

Voltage scan test settings

Voltage step [ ]

Sequence 1
Voltage Min A [ 0 ]
Voltage Max B [ $V_{max}$ ]
Voltage Min C [ 0 ]

Sequence 2
Voltage Min D [ 0 ]
Voltage Max E [ $-V_{max}$ ]
Voltage Min F [ 0 ]

Data analysis settings
Number of mirrors used for testing
[ 20 ]

[Start voltage scan]    [Save voltage scan]

Intensity Threshold
[ 160 ]    [Analyze scan results]

Alternative scan settings
Use Alt Voltage scan [X]

Min Voltage [ 0 ]         Voltage Step 1 [ 0 ]
Mid Voltage [ $V_{Mid}$ ]   Voltage Step 2 [ 0 ]
Max Voltage [ 0 ]

FIG. 15

PERFORMANCE ANALYSES OF MICROMIRROR DEVICES

TECHNICAL FIELD OF THE INVENTION

The present invention relates to the field of microelectromechanical devices, and more particularly to methods and apparatus of performance evaluations through measurements of electromechanical responses of the micromirror devices to driving forces.

BACKGROUND OF THE INVENTION

Microelectromechanical (MEMS) devices have found many applications in basic signal transductions. For example, MEMS-based spatial light modulators are transducers that modulate incident light in a spatial pattern in response to optical or electrical inputs. The incident light may be modulated in phase, intensity, polarization, or direction. This modulation may be accomplished through the use of a variety of materials exhibiting magneto-optic, electro-optic, or elastic properties. Such spatial light modulators have many applications, including optical information processing, display systems, and electrostatic printing.

A micromirror-based spatial light modulator is a spatial light modulator consists of an array of micromirrors. The mirror plates are individually addressable and deflectable with electrostatic fields so as to modulate incident light. A typical micromirror device comprises a deformable reflective mirror plate held by a deformable hinge such that the mirror plate can rotate to different positions in response to driving forces, such as electrostatic field. According to the different rotation positions, operation states, such as ON and OFF states in a binary operation mode are defined. In the ON state, incident light is reflected so as to produce a "bright" pixel on a display target, and in the OFF state, incident light is reflected to produce a "dark" pixel on the display target. In an application of displaying an image represented by image pixels having "bright" and "dark" values, the micromirrors are associated with the image pixels, and the micromirrors are individually set to the ON or OFF states according to the "bright" or "dark" values of the image pixels associated with micromirrors. The collective effect of the reflection from the micromirrors at the ON and OFF states for a given incident light is reproduction of the image on the display target. The same operation mechanism is applied to display applications for color images and videos. The color image display is often performed with a color wheel that generates the primary colors or the like. Video display applications are often performed with a sequential color field technique which requires the micromirrors be rotated rapidly and frequently between the ON and OFF state so as to reflect the appropriate "brightness" variation of the image pixels. In either application of image and video display applications, robust electromechanical responses to the driving forces and uniform ON and OFF states of the micromirrors are determinative factors for the evaluations of the product performance and quality.

Therefore, what is desired is a method and apparatus for measuring electromechanical responses of micromirror devices.

SUMMARY OF THE INVENTION

The objects and advantages of the present invention will be obvious, and in part appear hereafter and are accomplished by the present invention that provides a method and apparatus for operating pixels of spatial light modulators in display systems. Such objects of the invention are achieved in the features of the independent claims attached hereto. Preferred embodiments are characterized in the dependent claims. In the claims, only elements denoted by the words "means for" are intended to be interpreted as means plus function claims under 35 U.S.C. §112, the sixth paragraph.

BRIEF DESCRIPTION OF DRAWINGS

While the appended claims set forth the features of the present invention with particularity, the invention, together with its objects and advantages, may be best understood from the following detailed description taken in conjunction with the accompanying drawings of which:

FIG. 15 demonstratively illustrates a user-interface used for measuring the electromechanical responses of the micromirrors with selected voltage scanning schemes according to the invention.

DETAILED DESCRIPTION OF EXEMPLARY EMBODIMENTS

Figure 1:
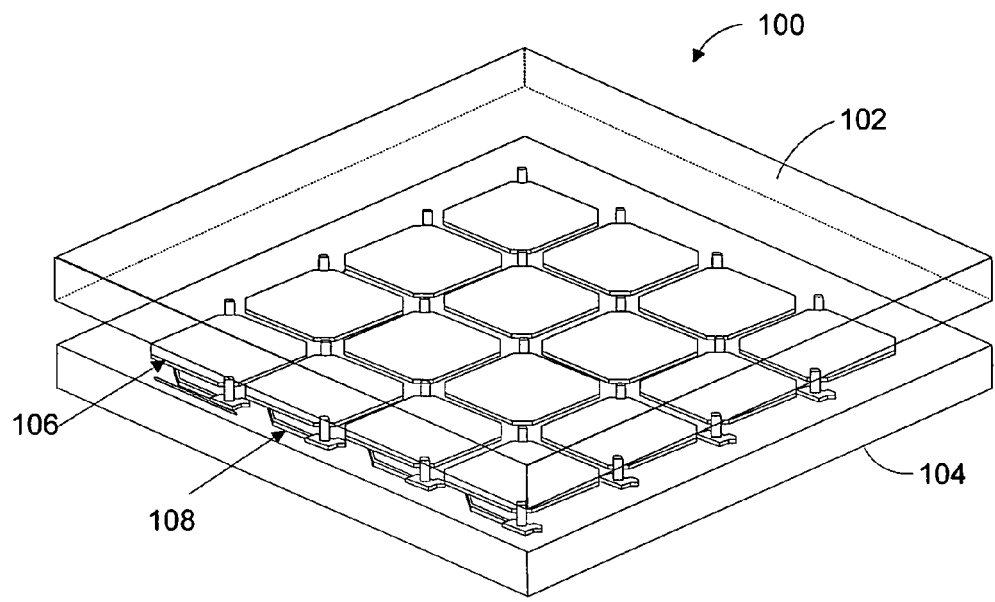
FIG. 1 is a perspective view of a portion of a micromirror array device in which embodiments of the invention can be implemented.

The invention provides a method and apparatus for evaluating the product quality and performances of micromirror array devices through measurements of the electromechanical responses of the individual micromirrors to the driving forces of electric fields. The electromechanical responses of the micromirrors according to the present invention are described in terms of the rotational angles associated with the operational states, such as the ON and OFF state angles of the ON and OFF state when the micromirror array device is operated in the binary-state mode, and the response speed (i.e. the time interval required for a micromirror device to transit form one state to another) of the individual micromirrors to the driving fields.

Specifically, a driving force is applied to the mirror plate of a micromirror being tested. In response, the mirror plate is deflected to different rotational angles determined by the amplitude and polarity of driving forces and the intrinsic mechanical and electrical properties of the micromirror being tested. The deflection of the mirror plate is monitored in a real-time fashion through the measurement of the intensities of the reflected light from the deflected mirror plate because the intensities of the reflected light are determined by the deflected positions of the individual mirror plates. And the dynamic variations of the intensities over time carry the information on the response speed of the mirror plate to the applied driving force. Therefore, from the intensities and the variation of the intensities of the reflected light, the electromechanical response of the micromirror to the driving force can be extracted. The same measurement can be conducted for all micromirrors of the micromirror array device, from which the electromechanical responses, such as the ON and OFF state angles and the response speed of all micromirrors of the micromirror array device can be obtained. Based on the extracted parameters, as well as predetermined criteria, the quality and performance of the microstructure device can be evaluated. For example, if all micromirrors of the micromirror array device have substantially the same ON and OFF state angle and substantially the same response speed, or the ON and OFF state angles and the response speed thereof have variations within respective predefined ranges, the micromirror array device may be acceptable as a "good" product. Otherwise, the micromirror array device is not acceptable and is marked as a "bad" product.

The measured electromechanical responses, in turn can be used as bases for optimizing the driving forces in practical operations of the microstructure devices. For example, the measurement results can be used to determine the optimum amplitudes and/or the profiles of the driving voltages for the micromirror array device in practical operations.

The corresponding experimental setup for measuring the electromechanical responses of the micromirror array device comprises an illumination system providing collimated light for illuminating the mirror plates of the micromirrors, an image capture device (e.g. a CCD device) for detecting intensities of the reflected light from the mirror plates of the micromirrors, and a set of optical elements for directing the light. A computing device having capacities of data process and control of other functional components of the experimental setup can also be provided for facilitating automated measurements in accordance with the methods of the invention. In particular, a plurality of program modules are constructed to perform the operations of, image analyses for determining the centers of the mirror plates, accepting parameters from the user for instructing controlling the applications of the driving forces to the mirror plates, analyzing the intensities of the reflected light from the mirror plates so as to extracting electromechanical response information of the individual micromirrors, and generating plots as appropriate. These program modules can be stored in and executed by the computer.

The measurement of the electromechanical responses of the micromirrors is preferably performed under a pressure lower than 1 atmosphere, such as around 20 Torr or less, or around 50 mTorr or less, or 15 mTorr or less.

In addition to micromirror devices, the present invention is applicable to other type of microelectromechanical devices having deflectable reflective planar members. For simplicity and demonstration purposes only, the present invention will be discussed with reference to a micromirror array device, such as a spatial light modulator having an array of micromirrors, each of which has a deflectable reflective mirror plate. Those skilled in the art will certainly appreciate that the following examples are not be interpreted as a limitation. Rather, other variations within the spirit of the invention are also applicable.

Turning to the drawings, FIG. 1 illustrates a perspective view of a portion of a micromirror array device 100. The micromirror array device comprises micromirror array 106 and electrode and circuitry array 108. Each micromirror has a mirror plate that is held by a hinge (e.g. a torsion hinge) such that the mirror plate can rotate along a rotation axis. According to an embodiment of the invention, the mirror plate of each micromirror can rotate from a natural resting state (e.g. parallel to the substrate) to 8° degrees or more, or 10° degrees or more, or 12° or more, or 14° degrees or more.

In this particular example, the micromirrors and electrodes and circuitry are formed on separate substrates. Specifically, the micromirrors are formed on substrate 102 that is light transmissive, such as glass, while the electrodes and circuitry are formed on substrate 104 that is a standard semiconductor wafer. The semiconductor wafer having the electrodes and circuitry is places proximate to the glass substrate having the micromirrors such that the mirror plate can be rotated by an electrostatic force established between the mirror plate and the electrode. Instead of on separate substrates, the micromirrors and the electrodes and circuitry can be formed on the same substrate, such as a semiconductor wafer. In another embodiment of the invention, the micromirror substrate can be formed on a transfer substrate that is light transmissive. Specifically, the micromirror plate can be formed on the transfer substrate and then the micromirror substrate along with the transfer substrate is attached to another substrate such as a light transmissive substrate followed by removal of the transfer substrate and patterning of the micromirror substrate to form the micromirror.

The micromirrors operate in binary-mode, that is, the mirror plates of the micromirrors switch between an ON and OFF state in performing the light modulation. In the ON state, the mirror plate of the micromirror reflects incident light so as to generate a "bright" pixel on a display target; and in the OFF state, the mirror plate reflects the incident light so as to generate a "dark" pixel on the display target. In a number of embodiments of the invention, the micromirror array is constructed having a pitch (the center-to-center distance between adjacent micromirrors) of 25 micrometers or less, or 10.16 micrometers or less, or from 4.38 to 10.16 micrometers. The gap between adjacent micromirrors is approximately of 0.5 micrometers or less, or from 0.1 to 0.5 micrometer. And the mirror plate of the micromirror has a dimension of from 20 micrometers to 10 micrometers.

For simplicity purposes, only 4×4 micromirrors are illustrated in the figure. Oftentimes, the micromirror array device has more micromirrors. For example, when the micromirror array device is a portion of a spatial light modulator of a display system, it may have millions of micromirrors, the number of which determines the resolution of the display system. For example, the spatial light modulator may have a resolution of 1024×768 or higher, or 1280×1024 or higher, or 1640×1280 or higher. Of course, the micromirror array device may have a fewer number of micromirrors than in display, or other applications.

The operations of the individual micromirrors are determined by the rotations of the individual mirror plates in response to the applied electrostatic forces. Such responses can be described in terms of the rotation angles of the mirror plates and the speeds of the responses to the electrostatic forces. The mirror plate rotates under an electrostatic force. For a given micromirror device, the angle that the mirror plate can be rotated is determined by the amplitude of the electrostatic field. When the micromirror is operate in a binary-state including the ON and OFF state, particular rotational angles are desired for the ON and OFF state. Accordingly, the electrostatic forces for driving the mirror plate to the ON and OFF state angles need to be determined. Moreover, the time characteristic of the mirror plate in transition from one state to another is also a critical factor, which determines the quality of the displayed images, especially the video images.

In order to evaluate the product quality and performance of the micromirror array device in terms of the electromechanical responses to the electrostatic forces, the dynamic rotational behaviors of the individual mirror plates in the presence of the driving forces are measured through the measurements of the intensities of the reflected light from the individual mirror plates, and the variations of the intensities over time, which will be discussed in detail in the following with reference to FIG. 2.

Figure 2:
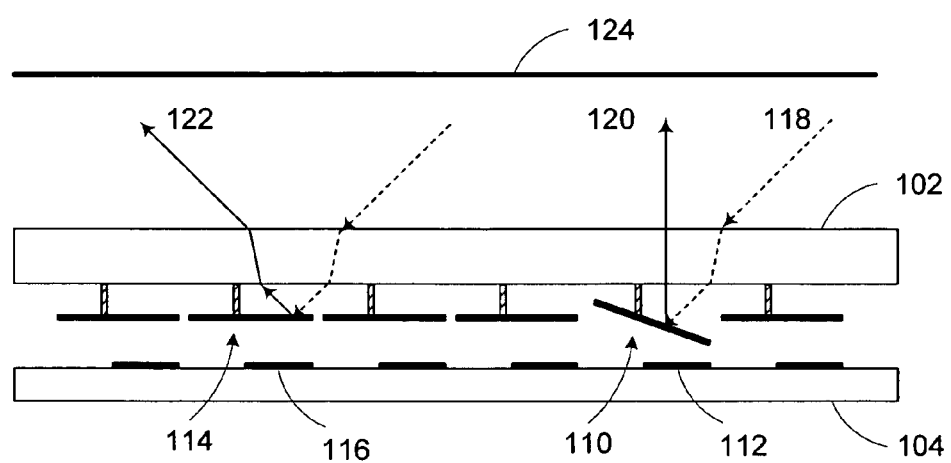
FIG. 2 is a cross-sectional view of a portion of the spatial light modulator in FIG. 1 with the mirror plates thereof at different rotation positions.

Referring to FIG. 2, the spatial light modulator in FIG. 1 is illustrated in a cross-sectional view. The deflectable reflective mirror plates are held by deformable hinges that are formed on glass substrate 102. Electrodes and circuitry (not shown) are formed on the semiconductor substrate 104 for deflecting the mirror plates. For example, the mirror plate of micromirror 110 can be rotated in a spatial direction by an electrostatic force established between the mirror plate and electrode 112 that is associated with the mirror plate. The collimated incident light 118 is redirected into reflected light 120 after reflection. Depending upon the incident angle of the light and the rotation angle of the mirror plate, reflected light can be along the perpendicular direction as shown in the figure. For a micromirror without application of the driving force, such as micromirror 114 having no electrostatic force established between the mirror plate thereof and electrode 116, the mirror plate is at the natural resting state, such as parallel to the substrate, as shown in the figure. The collimated incident light 118 is thus reflected to reflected light 122 that travels along a different direction from reflected light 120. On image capture device 124, such as a CCD device that is placed on top of the micromirrors, reflected light 120 generates a "bright" pixel, while reflected light generates a "dark" pixel. That is, the illumination intensity of the image generated by the reflected light 120 is higher than that of reflected light 122. In turn, the rotational positions of the mirror plates can be deducted from the intensities of the corresponding image on the image capture device.

Figure 3:
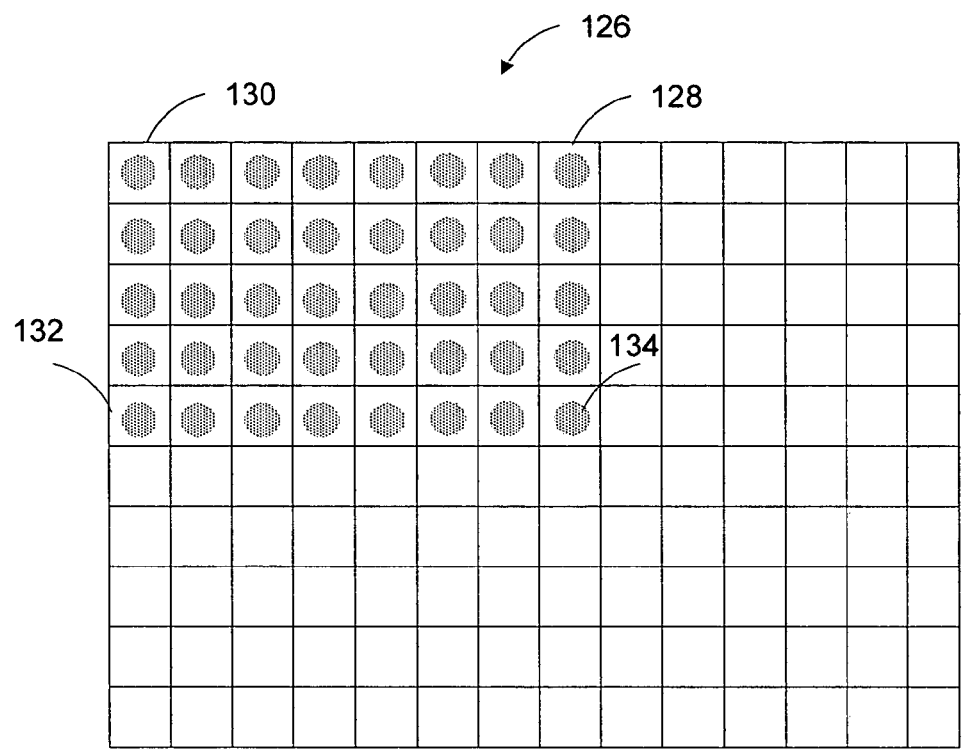
FIG. 3 demonstratively illustrates an exemplary image of a portion of the micromirrors in FIG. 1.

As a simplified example, FIG. 3 schematically illustrates a captured image of a set of micromirrors of the micromirror array device at a time. Each image cell (e.g. cells 130, 128, 132, and 134) is an image of a mirror plate and is generated by the reflected light from the mirror plate. When the micromirror is at the ON state, the corresponding image cell is "bright"; while the image cell is "dark" when the micromirror is at the OFF state. That is, the darkness of the image cell reflects the rotational positions of the mirror plate of the micromirror. For the particular example in the figure, the cells with the shaded solid circles have higher illumination intensities ("bright" image cells) than those otherwise. Accordingly, the mirror plates corresponding to the cells having the shaded solid circles are rotated to an angle of the ON state, whereas the mirror plates corresponding to the cells having no shaded circles stay at the OFF state. Specifically, the mirror plates corresponding to the cells within the matrix with the corners of 130, 128, 134, and 132 are in the ON state, and the remaining mirror plates are in the OFF state. In generating such an image, electrostatic fields are applied to the mirror plates individually for rotating the mirror plate. Because the ON and OFF rotational angles are determined by the amplitudes of the electrostatic forces; and the ON and OFF state angles can be monitored from the intensities of the image cells of the mirror plates, the ON and OFF state voltages can thus be associated with and deducted from the intensities of the image cells of the captured image. The voltages associated with the ON and OFF states are often referred to as the ON and OFF state voltages, respectively. Therefore, the ON and OFF state voltages can be measured from the measurements of the light intensities of the corresponding image cells.

In addition to the "brightness" of the image cells of the micromirrors, variation of the "brightness" of the image cells over time carries the information of the response speed of the micromirror to the electrostatic forces. For example, when a driving force is applied to the mirror plate of a micromirror at the OFF state, the mirror plate is rotated from the OFF state to the ON state. Accordingly, the image cell of the mirror plate changes from "dark" to "bright." Clearly, the speed of the mirror plate in transiting from the OFF to the ON state is associated with the time interval of the image cell changing from "dark" to "bright."

Figure 4:
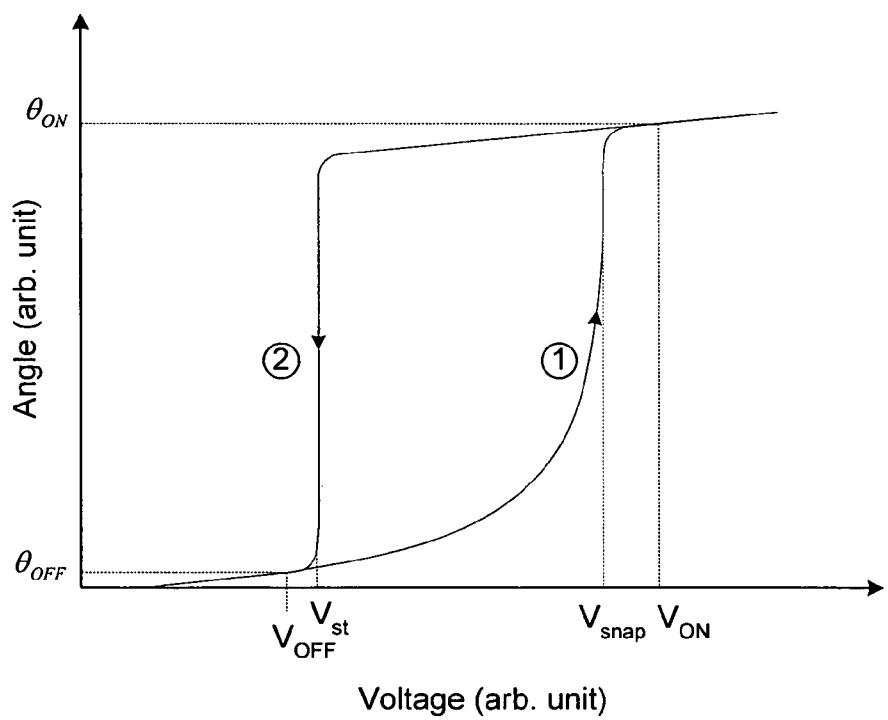
FIG. 4 schematically illustrates a typical electromechanical response curve of a micromirror device in FIG. 1.

With a given electrostatic force, the mirror plate has certain response capability. FIG. 4 plots the rotation angles vs. the voltage applied to the mirror plate of a typical micromirror device. Both axes in the plot are in arbitrary units. During the course of upwards voltage sweeping from zero (0) voltage, the rotation angle increases with the increase of the voltage along branch ①. At voltage $V_{snap}$, the mirror plate rotates to an angle of $\theta_{snap}$. Above $V_{snap}$, the rotation angle starts to saturate. In general, the ON state voltage is defined as a small amount higher than the $V_{snap}$, and the corresponding rotation angle is defined as the ON state angle $\theta_{ON}$. During the course of downwards voltage sweeping from $V_{ON}$, response hysteresis occurs. Specifically, the rotation angle decreases with the decrease of the voltage but along branch ②. Around $V_{st}$, the rotation angle drops to a value after which the rotation angle starts to decrease slowly. In general, the OFF state voltage can be defined as a small amount lower than voltage $V_{st}$.

Figure 5:
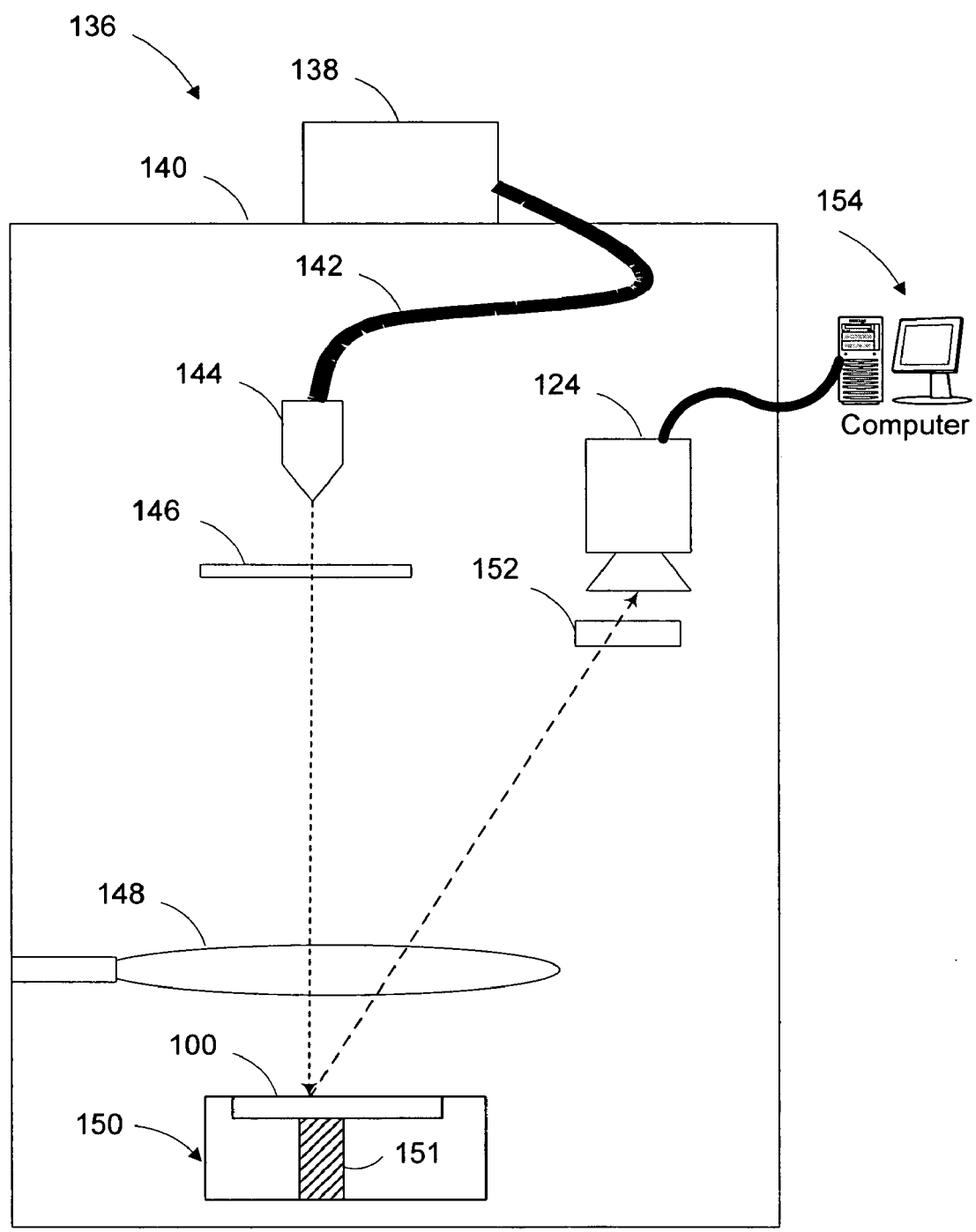
FIG. 5 schematically illustrates an experimental setup for measuring the electromechanical responses of the micromirror array device in FIG. 1 according to an embodiment of the invention.

In order to determining the responses of the individual micromirrors to driving electrostatic forces, an experiment setup according to an embodiment of the invention is provided. Referring to FIG. 5, an exemplary experimental setup for performing the method of the present invention is schematically illustrated. System 136 comprises light source 138 with attached fiber optic cable 142 connected to microscope objective 144, neutral density filter 146, diffuser 152, condenser lens 148, vacuum chamber 150 in which micromirror device 100 is placed, sample holder 151, image capture device 124, and computing device 154. The light source can be DC bulbs (e.g. halogen light bulbs) or LED or other type of light sources. The vacuum chunk may be connected to appropriate vacuum instruments, such as pumps and valves. Sample holder 151 can be constructed in any suitable forms. For example, the sample holder can be a flat surface on which the sample device can be attached and held. The sample holder can also have a supporting surface on which the sample device to be measured can be attached and hold. The supporting surface is preferably movable 3-dimentionally. For example, in addition to the ability of moving in the X-Y plane, the supporting surface can be tilted at any desired angles. In this way, the sample device attached to the supporting surface can be rotated. In particular, the reflective surface of the sample device can be tilted as desired—facilitating adjustment of the propagation direction of the reflected light. Moreover, the sample holder can be equipped with an automation system, such as a motor, along with a position detector. In this way, the movement of the supporting surface of the sample holder can be automated, and the position of the supporting surface can be determined precisely.

In accordance with an embodiment of the invention, the components of the system in FIG. 5 are arranged according to the configuration of the device to be measured. For example, when a micromirror array device having an array of deflectable reflective mirror plates is to be measured, the image capture device is desired to be positioned in the propagation path of the reflected light when the mirror plates are at a particular state. For example, mirror plate can rotate to an ON state angle and an OFF state angle, or not rotated (e.g. parallel to the substrate on which the micromirror is formed). The image capture device can thus be positioned in the propagation path of the reflected light from the mirror plate at the ON state angle, the OFF state angle or parallel to the substrate. When the image capture device is positioned in the propagation path of the reflected light from the mirror plate at the ON state, the detected illumination intensity of the reflected light will increase as the mirror plate rotates towards the ON state angle. When the photodetector is positioned in the propagation path of the reflected light from the mirror plate parallel to the substrate, the detected illumination intensity decreases as the mirror plate rotates towards the ON state angle. As a way of example, the image capture device can be positioned at a location wherein an imaginary line connecting the device to be measure has an angle to the incident illumination light, wherein the angle can be 0° degree, 10° degrees or more, 12° degrees or more, 14° degrees or more, 16° degrees or more, 18° degrees or more, 20° degrees or more, and 22° degrees or more.

The light source emits a beam of light for the measurement system. The light has a wavelength substantially less than the minimum dimensions of the mirror plate. The light from the light source is conducted to the microscope objective through the fiber optic cable. The microscope objective forms a point light source and emitting light passing through the diffuser. The condensing lens preferably having a 6" or 8" diameter collimates the diffused light and illuminates the micromirror device within the vacuum chamber. The incident light onto the micromirror device is reflected by the mirror plates of the micromirrors. The reflected light passes through the neutral density filter and is collected by the condensing lens and focused into the image capture device. The image capture device can be a display target, a CCD, or any other type of devices having the function of capturing images.

Operations of the functional members of the system, such as the vacuum chamber and the associated vacuum instruments, the image capture device and the optical elements, can be controlled by computing device 154 that has appropriate computer-executable instructions for performing the controlling, which will be discussed afterwards. Specifically, the computing device can generate instructions for adjusting the relative positions of the illumination system (e.g. light objective 144), the micromirror device in the vacuum chamber, and the image capture device such that each and every regions of the micromirror device can be illuminated, and the reflected light such each and every regions can be captured by the image capture device. In this embodiment, a motorized stage can be attached to the micromirror device so as to smoothly and accurately move the micromirror device. Moreover, the computing device has a connection to the image capture device for retrieving the image data from the image capture device and then analyzing the image data.

The method of the present invention can be implemented in many ways. In the following, an exemplary procedure according to the method of the invention for measuring the dynamic electromechanical response of the micromirrors will be discussed with reference to FIGS. 6 through 12. The procedure can also be implemented in the computing device for being automatically executed. For this purposes, a set of programmable functional modules are provided for interfacing the user, which will be discussed in detail afterwards with reference to FIGS. 13 through 15.

Figure 6:
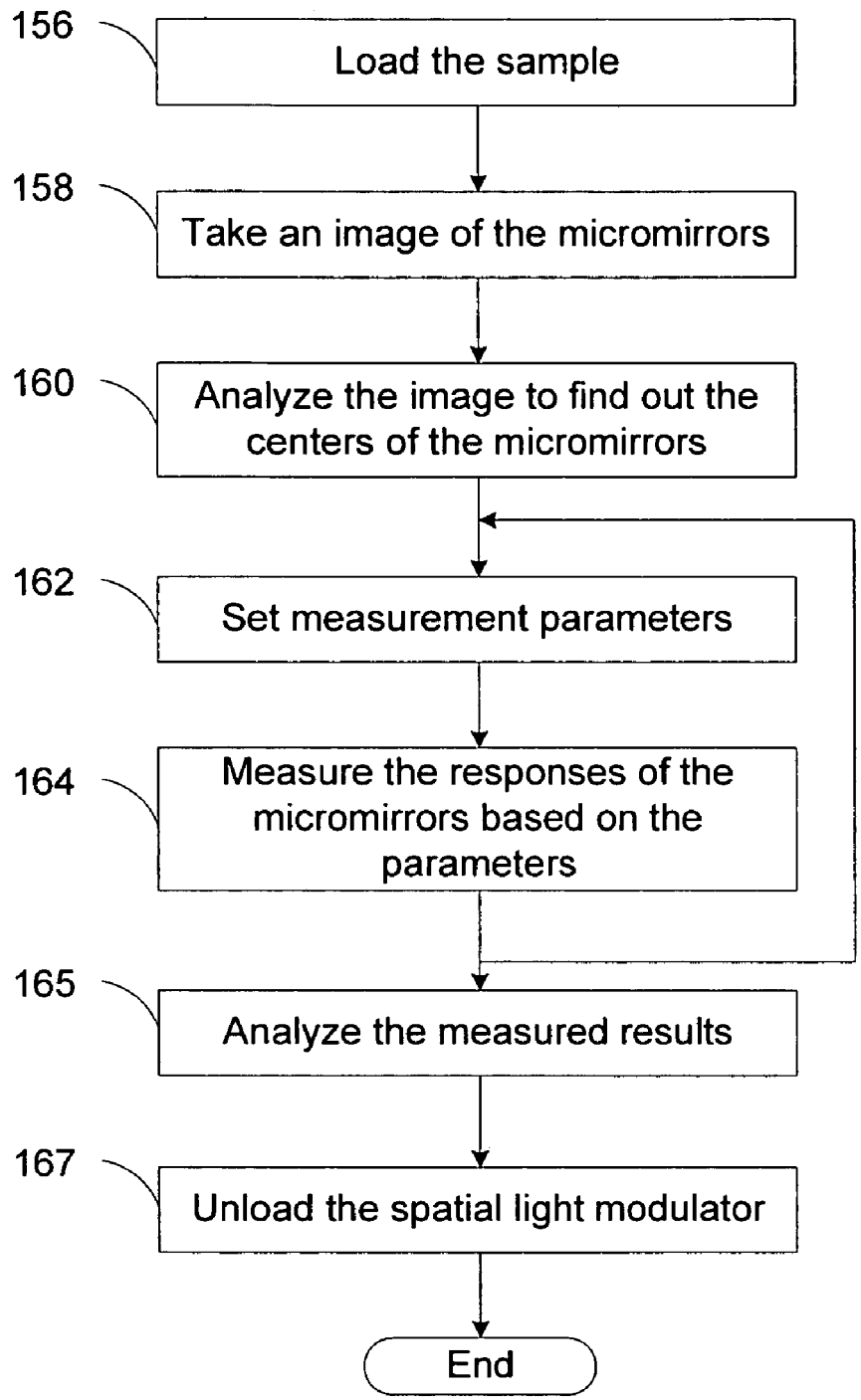
FIG. 6 is a flow chart showing the steps executed for measuring the electromechanical responses of the micromirrors in FIG. 1 according to the embodiment of the invention.

FIG. 6 is a flow chart presents the steps executed for performing the measurement procedure according to the method of the invention. The procedure starts from loading the micromirror device into the measurement system (step 156). In fact, more than one spatial light modulators, such as 16 or more spatial light modulators can be loaded into the system at a measurement with each spatial light modulator has an array of micromirrors. Before loading, the micromirror device may have passed one or more inspections, such as inspection with naked eyes, or other uniformity inspections, as set forth in U.S. patent application Ser. No. 10/875,602 "A Method and Apparatus for Quantitatively Analyzing Uniformity in Microelectromechanical Devices", and U.S. patent application Ser. No. 10/875,555 now U.S. Pat. No. 7,345,806 "A Method and Apparatus for Characterizing Microelectromechanical Devices on Wafers", both are filed on the same day as the current patent application, and the subject matter of each being incorporated herein by reference.

Figure 7A:
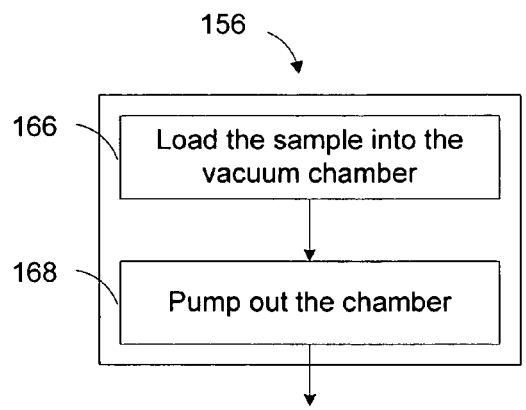
FIG. 7a is a flow chart showing the steps executed for loading the micromirror array device into the experimental setup.

In order to individually drive the micromirrors with electrostatic forces during measurements, the micromirrors are connected to appropriate driving circuits that may be embedded within the measurement system or installed outside the measurement system. The loading step may have further steps, as shown in FIG. 7a.

Referring to FIG. 7, the micromirrors are loaded into the vacuum chamber (e.g. vacuum chamber 150 in FIG. 5) (step 166). According to an embodiment of the invention, the measurement is preferably performed within an environment having a pressure under 1 atmosphere, more preferably around 20 Torr or less, or 50 mTorr or less, or 15 mTorr or less. This is performed at step 168, in which step the vacuum chamber is pumped out to the desired pressure.

Referring back to FIG. 6, after the micromirrors to be measured are securely installed in the measurement system with the desired pressure, an image of the micromirrors is taken by the image capture device (step 158). In taking the image, all micromirrors in the inspection area are turned to the ON state such that the cells corresponding to the micromirrors under inspection have certain level of illumination intensities. As in the example in FIG. 3, the micromirrors corresponding to the cells within the matrix having the corners 128, 130, 132, and 134 are under inspection at a time. Though as illustrated therein for simplicity and demonstration purposes only, the number of micromirrors under inspection (i.e. inspected simultaneously) at a time can be 35×35 or more, or 128×92 or more. Given the inspection region, the locations of the micromirrors in the inspection region are precisely determined and recorded (step 160 in FIG. 6). For this purposes, the centers of the mirror plates of the micromirrors in the inspection region are determined.

The centers of the micromirrors can be determined in many ways. As a way of example, FIG. 7c shows the steps execute in finding the centers of the image cells of the micromirrors in the inspection region. Starting from step 192, the edges of the image cells of the individual micromirrors are calculated. The edge detection of an image can be accomplished in many ways. According to an embodiment of the invention, a Siebel operator is applied to the captured image for the purposes of edge detection. After the edge detection, both horizontal and vertical edges of the image cells corresponding to the micromirrors are obtained. Following the edge detection, noise filtering step 194 can be optionally performed so as to remove or reduce the noise of the image. According to the embodiment of the invention, the image is further processed in the Fourier space. Therefore, a Fourier transformation is applied to the image at step 196. In the Fourier space, the peaks of the image are located (step 198). Given the peak positions, the pitches and rotation angles of the mirror plates are calculated in the Fourier space (step 200) with the pitch sizes include both pitch sizes along vertical and horizontal directions. Such calculated pitch sizes may be different at different locations in the image. As an optional feature, a plurality of pitch sizes at different locations of the image can be calculated and then averaged. Such averaged pitch size can be used as the pitch sizes of the entire micromirror array. Specifically, the image is divided into sub-images (step 202). Then the pitch sizes in the sub-images are averaged at step 204. With the calculated pitch sizes and the detected edges of the image cells of the individual micromirrors, the geometric centers are determined at steps 208 and 210. According to the embodiment, the geometric center detection is performed in the real-space. Therefore, the Siebel transformation following the Fourier transformation is applied to the image so as to transform the image from the Fourier space back into the real-space (step 206). At step 207, the geometric centers are detected. Given the geometric centers, the edges, and the pitch sizes of the image cells of the individual micromirrors, the positions of the centers of all micromirrors of the micromirror array device in the measurement system can be calculated (step 210).

Given the coordinates of the centers of the mirror plates (micromirrors), each mirror plates in the inspection region can be precisely located. In particular, the rotation positions of the mirror plate can be derived from the illumination intensities at the centers of the corresponding images, as shown by the shaded solid circles in FIG. 3. Moreover, the micromirrors being inspected can be individually identified.

Figure 7B:
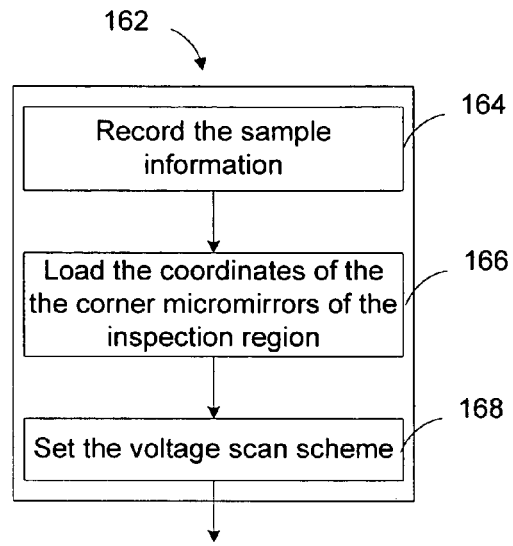
FIG. 7b is a flow chart showing the steps executed for setting the measurement parameters.
Figure 7C:
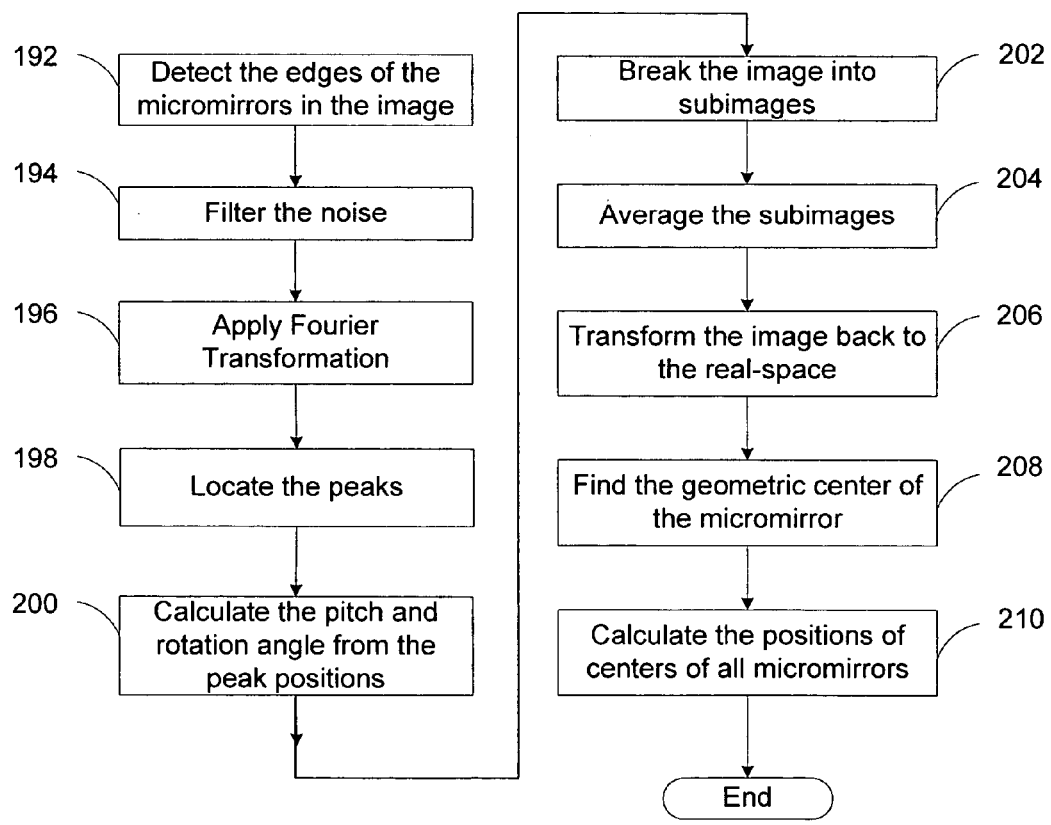
FIG. 7C is a flow chart showing the steps executed for detecting the geometric centers of the individual micromirrors of the micromirror array device.

Returning back to FIG. 6, following the image analyses for determining the centers of the micromirrors, a set of measurement parameters are determined (step 162), which is more detailed in FIG. 7b. Referring to FIG. 7b, information on the micromirrors, such as the identification number(s) is made of record (step 164). The coordinates of the micromirrors at the corners of the inspection region are saved such that each micromirror in the inspection region can be located. In the example of the image as shown in FIG. 3, the coordinates of the micromirrors 128, 130, 132, and 134 are recorded. When combined with other parameters, such as the pitch sizes along the column and row, the coordinates of each micromirror in the inspection region can then be determined. This is of particular importance when the measurement is to be performed automatically with the computing device, in which case, the computing device is capable of measuring the micromirrors sequentially based on the coordinates of the micromirrors.

In order to measure the dynamic responses of the individual micromirrors, a suitable voltage scan scheme is selected (step 168). The scheme defines the voltage scan profile and related parameters. For demonstration purposes, four (4) different voltage-scan schemes targeting at detecting different aspects of the dynamic responses of the micromirrors to the driving electrostatic forces will be described in the following. It will be appreciate that other suitable voltage scan schemes without departing from the spirit of the invention are also applicable. For example, a voltage scan scheme combining the two or more of the following discussed voltage scan schemes or the like are applicable.

Figure 8:
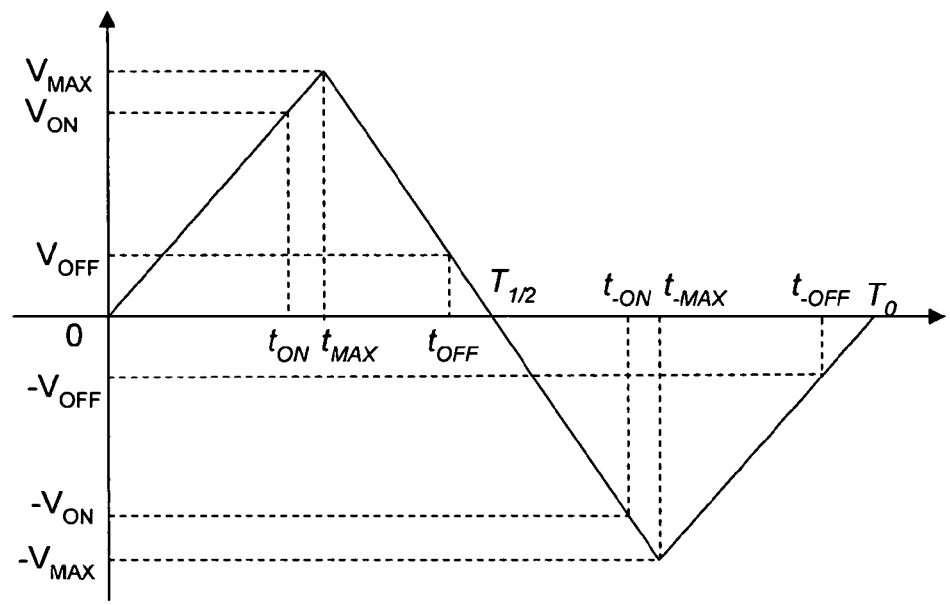
FIG. 8 demonstratively illustrates a voltage profile of a voltage scanning scheme for use in measuring the electromechanical responses of the micromirrors according to an embodiment of the invention.

FIG. 8 illustrates a voltage scan profile of a static scan scheme according to an embodiment of the invention. This scan profile is particular useful for measuring the ON and OFF state angle of the micromirror. The profile comprises a positive voltage increase edge from time $0$ to $t_{Max}$ followed by a positive voltage decrease edge from time $t_{Max}$ to $T_{1/2}$. The two edges may or may not be symmetric along the $t_{max}$ axis. As an optional feature, the profile may also comprise a negative voltage increase edge from time $T_{1/2}$ to $t_{-Max}$ followed by a negative voltage decrease edge from time $t-_{max}$ to $T_0$. Similarly, the two edges may or may not be symmetric along the $t-_{max}$ axis. However, it is preferred that the triangular voltage profiles $0-V_{max}-T_{1/2}$ and $T_{1/2}-(-V_{Max})-T_0$ are symmetric around the point $(T=T_{1/2}, V=0)$, even though not required. As a way of example, $t_{max}$ can be from 3 to 10 sec, or from 10 sec to 50 sec, or from 50 to 100 sec, or from 100 to 200 sec or more. $V_{max}$ can be from 10 to 25 volts, or from 25 to 45 volts, or from 45 to 100 volts, or more.

During the voltage sweeping from $T=0$ to $T=T_0$, the illumination intensity of the image cell corresponding to the mirror plate to which the voltage is applied is monitored in the real-time fashion. For the variation of the illumination intensity, the rotation position of the mirror plate is thus dynamically detected. Specifically, when the mirror plate is rotated to the ON state angle, the illumination intensity is maximized. To obtain the voltage for the ON state angle of the micromirror, the voltage is swept upwards from $V=0$ at $T=0$. When then voltage reaches to $V=V_{on}$ at time $t_{ON}$, it is observed that the illumination intensity is maximized. Therefore, such voltage $V_{on}$ is defined as the ON state voltage. For security reasons, the voltage can be further increased a small amount to $V_{Max}$ at time $t_{Max}$. The voltage is then swept downwards from $V=V_{max}$ at $T=t_{max}$. At $V=V_{off}$ at time $T=t_{off}$, it is observed that the illumination intensity of the image cell corresponding to the mirror plate is minimized. It is indicated that the mirror plate is turned to the OFF state, such as a state when the mirror plate is in the natural resting state or parallel to the substrate. Such a voltage $V_{OFF}$ is defined as the voltage corresponding to the OFF state. For further ensuring that the mirror plate is returned to the OFF state, the voltage is decreased a small amount further, such as to $V=0$ at $T=T_{1/2}$. In the above voltage scanning scheme, a positive voltage is applied to the mirror plate to rotate the mirror plate. In contrast, a negative voltage can also be applied to the mirror plate to achieve the same effect. Specifically, the voltage sweeping can be continued at time $T=T_{1/2}$ towards the negative direction. When the negative sweeping voltage reaches $V=-V_{ON}$ at time $T=t_{-on}$, it is observed that the illumination intensity of the image cell corresponding to the mirror plate is maximized. Accordingly, voltage $V=V_{-ON}$ is defined as the voltage for the OFF state. The voltage is swept a small amount further to $V_{max}$ at time $T=T_{-max}$ to ensure the definition of the OFF state voltage. The sweeping voltage is then swept downwards at time $T=t_{-max}$. When the sweeping voltage is at $V=-V_{off}$, it is observed that the illumination intensity of the image cell corresponding to the mirror plate is minimized. Such voltage is then defined as the voltage for the OFF state. For ensuring the defined voltage for the OFF state, the sweeping voltage is swept a small amount further such as $V=0$ at $T=T_0$.

The observed ON and OFF state voltages in different sweeping directions can be compared so as to obtain the electromechanical property of the micromirror. An ideal micromirror is expected to have symmetric ON and OFF state voltages. Specifically, the ON state voltage $V_{on}$ obtained from the positive voltage sweeping has the same absolute value as the ON state voltage obtained from the negative voltage sweeping. That is $|V_{on}|=|-V_{on}|$. The same for the OFF state voltages, $|V_{off}|=|-V_{off}|$.

The measurement is then repeated for the remaining micromirrors in the inspection region. After the measurements of the micromirrors in one inspection region, the inspection region is shifted to cover another group of micromirrors followed by the measurements. The measurement process is repeated until the desired electromechanical responses of all micromirrors in the spatial light modulator are obtained. After the completion of the measurement of one spatial light modulator, the measurement can be continued on another spatial light modulator. Specifically, multiple spatial light modulators can be placed in the measurement system as shown in FIG. 5 according to an embodiment of the invention. This is of particular importance when the measurement is performed in a vacuum chamber (e.g. vacuum chamber 150 in FIG. 5), because in this way, the measurement can be continuously performed for all the spatial light modulators without extra efforts in reloading spatial light modulators after each measurement.

With the measured electromechanical responses (e.g. the ON and OFF state voltages) of the micromirrors in a spatial light modulator, the quality and performance can be evaluated. Specifically, if all micromirrors have the same ON and OFF state voltage, or the variation of the ON and/or OFF state voltages is within a predefined range, it can be said that the micromirror array device is acceptable. Otherwise, the micromirror array device is an inferior product, which can be discarded.

The measured ON and OFF state voltages, in turn, can be used for calibrating and optimizing the driving voltages for a quality product of the micromirror array device in operation. According to the invention, the ON state voltage ($V_{on}$) for driving the micromirrors in operation is calculated from the measured ON state voltages such that the mirror plate has the "fastest" response to the driving force $V_{on}$. To accomplish this, the response speed of the mirror plate needs to be measured, which will be discussed afterwards.

Figure 9:
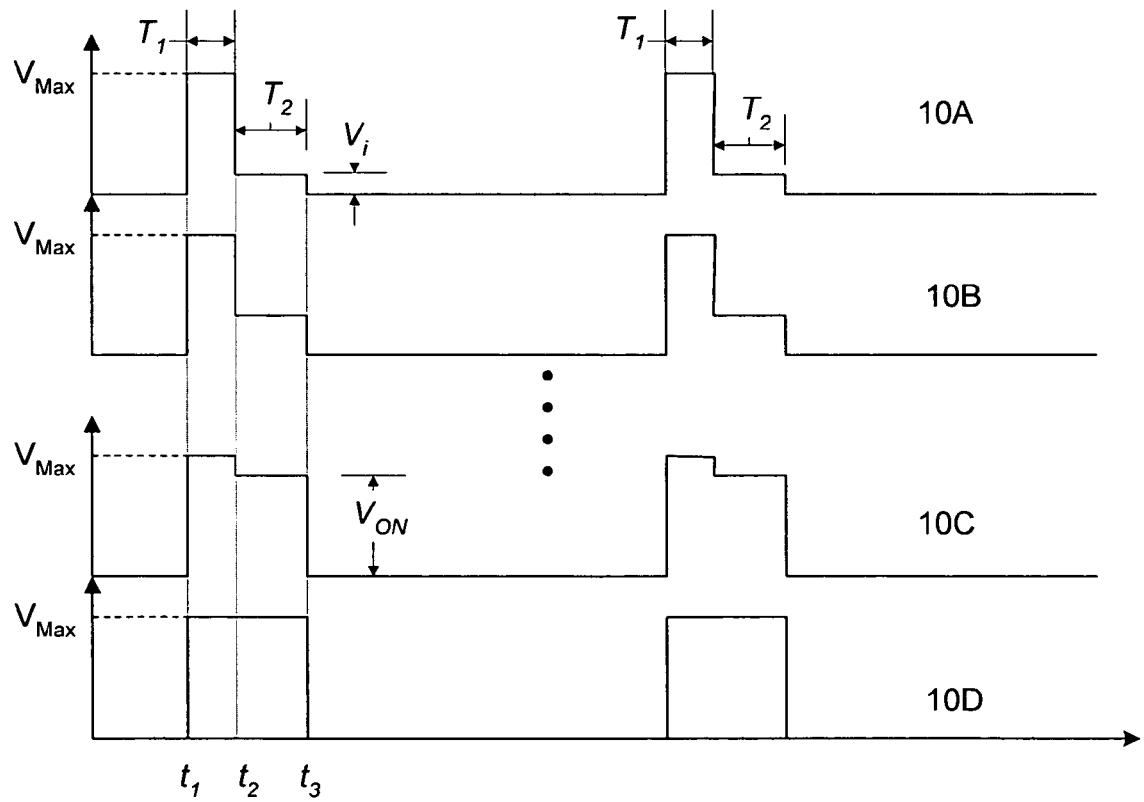
FIG. 9 demonstratively illustrates a voltage scanning scheme having a set of voltage sequences for use in measuring the electromechanical responses of the micromirrors according to another embodiment of the invention.

In addition to the driving voltage profile in FIG. 8, the dynamic electromechanical response of the micromirrors can also be measured with other driving voltage scan schemes, such as that shown in FIG. 9. Referring to FIG. 9, the voltage scan scheme comprises a set of driving voltage sequences, 10A, 10B, 10C, and 10D and many other similar sequences (not shown in the figure). Each voltage sequence comprises a set of pulse structures (duty cycles) each of which further comprises a peak having a width of $T_1$ followed by another peak with a width of $T_2$. Both $T_1$ and $T_2$ are longer than the required time for the mirror plate to rotate to the ON state. The peak $T_1$ has a height of $V_{max}$ equivalent to the $V_{max}$ in FIG. 8. This peak is designated for pulling the mirror plate of the micromirror being tested to the maximum angle of the mirror plate. The peak of $T_2$ immediately following the peak $T_1$ has a height varying over time. The voltage increment of the peak at $T_2$ can be of any suitable value depending upon the desired precision, such as 1% or less of $V_{max}$.

During each duty cycle of a voltage sequence, the mirror plate is pulled to its maximum rotation angle by the voltage pulse at $T_1$. At time $t_2$, the voltage on the mirror plate drops to $V_i$ and remains at the mirror plate for a time period of $T_2$. If the voltage $V_i$ is less than the voltage required to rotate the mirror plate to the ON state, the mirror plate departs from the ON state to its natural resting state. In the corresponding image cell, the illumination intensity decreases. However, when the voltage $V_i$ during $T_2$ reaches or is larger than the ON state voltage, the mirror plate stays at the ON state. Accordingly, the illumination intensity of the image cell remains the same. From such measurement, the ON state voltage can be obtained.

As a way of example, voltage sequences 10A to 10D are applied to the mirror plate of the micromirror being tested. The voltage pulse at $T_2$ of each duty cycle in the sequences before 10C is less than the ON state voltage. The voltage pulse at $T_2$ of sequence 10C is equal to the ON state voltage, and the voltage pulse at $T_2$ of each duty cycle in the sequences after sequence 10C is larger than the ON stage voltage. The voltage sequences can be applied sequentially to the micromirror starting from sequence 10A. Because the voltage pulses at $T_2$ are less than the ON state voltage, the illumination intensity of the image cell corresponding to the micromirror being tested decreases during time periods $T_2$ when the voltage sequences 10A to 10B are applied. When the voltage sequence 10C is applied, the illumination intensity of the image cell changes during $T_2$ time intervals, indicating that the voltage at $T_2$ is equal to or larger than the ON state voltage. If the increment of the voltage at $T_2$ of sequence 10C from that in the applied voltage immediately prior to sequence 10C is small enough, the voltage at $T_2$ of sequence 10C is substantially the ON state voltage. For ensuring that the voltage at $T_2$ of sequence 10C is the ON state voltage, additional voltage sequences 10D can be applied.

In accordance with another embodiment of the invention, the voltage sweeping scheme can be inversed. Specifically, instead of applying the above voltage sequences in an increased order of the peak at $T_2$, the sequences can be applied in a decreased order. For example, sequence 10D can be applied before sequence 10C that can be followed by sequences 10B and 10A and other sequences consecutively.

Figure 10:
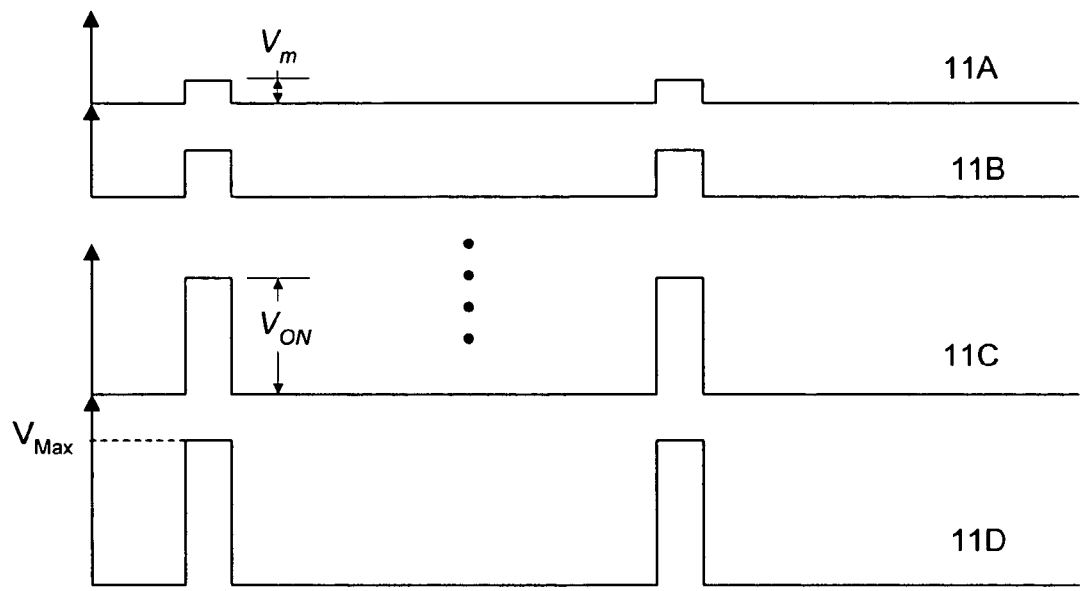
FIG. 10 demonstratively illustrates another voltage scanning scheme having a set of voltage sequences for use in measuring the electromechanical responses of the micromirrors according to yet another embodiment of the invention.

Referring to FIG. 10, another voltage scanning scheme for measuring the electromechanical responses of the micromirrors is illustrated therein. According to the scheme, voltage pulses of different voltages values are sequentially applied to the mirror plate of the micromirror being tested. Specifically, the scheme consists of a set of voltage sequences, and different sequences have voltage pulses of different values. The voltage sequences can be applied to the mirror plate in an increased or a decreased order of the voltages. For example, the scheme consists of voltage sequences 11A, 11B, 11C, and 11D. The voltage pulses $V_m$ in 11A is less than those in other sequences. The voltage pulses in 11B are higher than that in 11A, but lower than those in 11C and 11D. For simplicity and demonstration purposes, only four (4) voltage sequences are presented in FIG. 11. In practical, more voltage sequences can be provided and applied in an appropriate order. In fact, the total number of the voltage sequence depends upon the desired precision.

As a way of example, the voltage sequences can be applied to the mirror plate in an order of 11A, 11B, 11C, and 11D with the voltage values increased. Assuming that before the application of sequence 11C (i.e. during the applications of sequences 11A and 11B), the illumination intensities of the image cell corresponding to micromirror being tested yield a "dark" image, whereas the application of sequence 11C results in a "bright" image cell. It can then be determined that the ON state voltage of the micromirror is the voltage $V_{ON}$ in sequence 11C. Because the voltage sequences are applied to the micromirrors with the voltages thereof increased, the micromirror responses to the sequences of voltages along branch ① in FIG. 4. The voltage sequences can also be applied in an inversed order, such as from 11D to 11C, then 11B followed by 11A.

The ON and OFF state voltages describe one aspect of the electromechanical response of a micromirror. Another aspect of the electromechanical response of a micromirror can be described in terms of the response speed to the ON and OFF state voltages. Specifically, the response speed measures the time interval of the micromirror in transition from one state to another under a given driving voltage (e.g. the ON state voltage). According to an embodiment of the invention, the speed response can be measured with a voltage scanning scheme having a voltage scanning profile as shown in FIG. 11.

Figure 11:
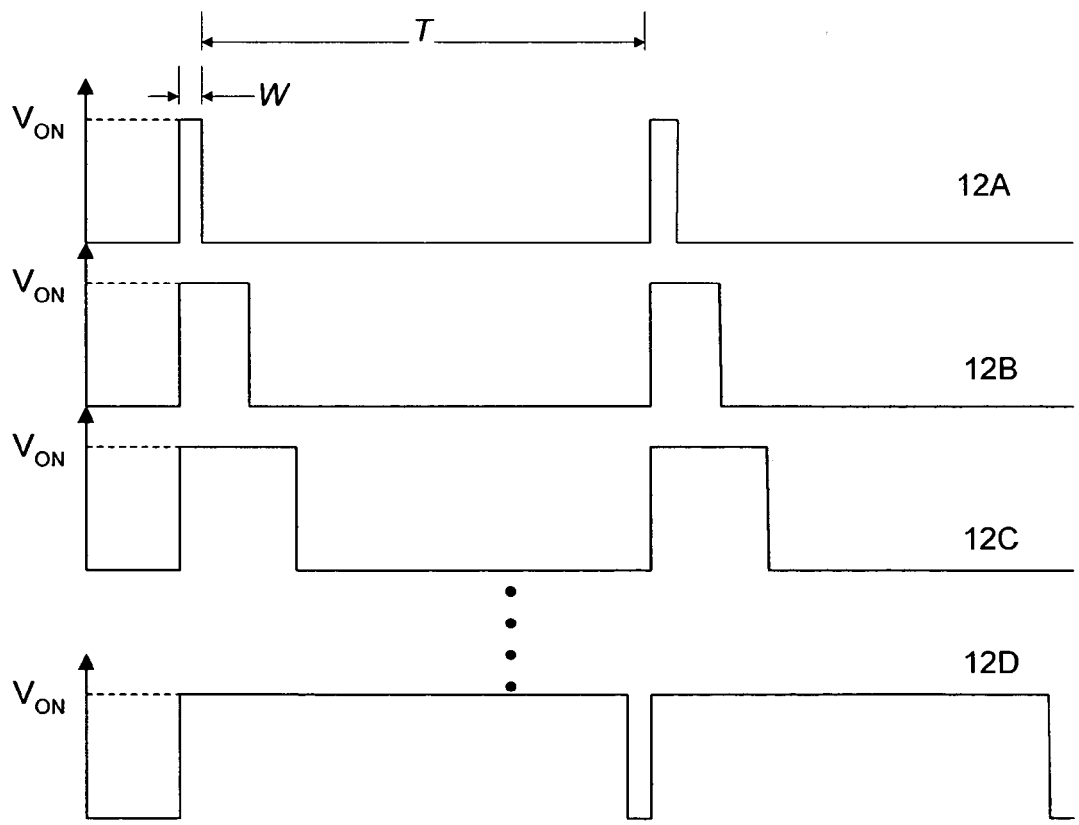
FIG. 11 demonstratively illustrates yet another voltage scanning scheme having a set of voltage sequences for use in measuring the electromechanical responses of the micromirrors according to yet another embodiment of the invention.

Referring to FIG. 11, the voltage scanning scheme consists of a set of voltage sequences, such as 12A, 12B, 12C, and 12D. The voltage pluses may have the same height, such as $V_{on}$ or $V_{max}$. The period T, thus the frequency of the voltage pulses is the same for all voltage sequences. In one voltage sequence, the widths of the voltage pulses W are the same. But the widths are different in different voltage sequences. The increment of the W for the voltage sequences consecutively applied to the micromirror is predetermined, such as 1% or less of the applied maximum voltage $V_{max}$.

In a typical measurement with the driving voltages shown in FIG. 11, the voltage sequences are applied to the mirror plate being tested, while the illumination intensity of the image cell corresponding to the micromirror is monitored at the same time. As a way of example, assuming the speed response of the micromirror corresponds to the voltage pulse width W of the voltage sequence 12C, voltage sequences (e.g. 12A and 12B) having the pulse widths less than that of sequence 12C will result in a "dark" image cell of the micromirror. When the voltage sequence 12C is applied to the micromirror, it is observed that the illumination intensity of the image cell of the micromirror is maximized, resulting in a "bright" image cell. For ensuring that the natural speed response of the micromirror corresponds to the pulse width W of voltage sequence 12C, additional voltage sequences, such as 12D can be applied to the micromirror in test, wherein the pulse width of sequence 12D is larger than that of sequence 12C. It should be point that, the four (4) voltage sequences in the figure are presented therein for demonstration and simplicity purposes only. In practice, more voltage sequences can be provided and applied to the micromirror, for example, between sequences 12A and 12C, and between sequences 12C and 12D.

After obtaining the speed responses of one micromirror, the same measurement is performed for another in the inspection region and the remaining micromirrors sequentially. Moreover, the same measurement procedure is carried out for another group of micromirrors in the spatial light modulator after the completion of the measurement in one inspection area until all the micromirrors of the spatial light modulator are tested. Because the measurement system as shown in FIG. 5 allows for loading multiple spatial light modulators (e.g. six) at one time, the measurement can be continued for the rest spatial light modulators.

Returning to FIG. 8, the voltage scan scheme is selected (e.g. from the schemes as discussed above with references to FIGS. 8 through 11) at step 168 of step 162 in FIG. 6. Returning back to FIG. 6, the dynamic electromechanical responses of the micromirrors are then measured at step 164 according to the parameters set at step 162. Following the measurements, the measurement results are then analyzed (step 165) so as to obtain the quantitative descriptions of the electromechanical responses of the micromirrors, such as the ON and OFF state angles, the ON and OFF state voltages ($V_{on}$ and $V_{off}$) and the response speed of the micromirrors under given driving voltages. In particular, an ON state voltage $V_{on}$ is obtained from the quantitative descriptions such that the micromirrors of the micromirror array device have the "fastest" response under $V_{on}$ in average. The analyze step (step 165) can be conducted after the completion of the measurements for the micromirrors of the entire micromirror array device. Alternatively, the measurements can be conducted during the measurement. For example, the analysis can be performed after each measurement of a micromirror, or after the measurements of a group of micromirrors (e.g. the micromirrors in the inspection region), or after the measurements of the micromirrors of the entire micromirror array device, or at a later time after the measurements.

The measurement procedure may loop back to step 162 for performing the measurements for another group of micromirrors of the micromirror array device, or for the micromirrors on another micromirror array device in the measurement system until all the micromirrors of all desired micromirror array devices are measured.

After the completion of the measurements, the micromirror array devices are unloaded from the measurement system (step 167). In performing the unloading, the vacuum chamber of the measurement system is vented before unloading.

In the above discussion, a homogeneous illumination light beam incident onto the micromirrors is preferred. However, such homogeneous light beam may not always be ready. When an inhomogeneous light beam is used for illuminating the system, reflected light from the mirror plates of the micromirrors will not be homogeneous either, and the accuracy of the measured light intensities from the individual micromirrors can be degraded. Moreover, the intensities of the reflected light from the micromirrors may be out of the acceptable range of the photodetector, in which way, the detected illumination intensity of the reflected light will not be accurate. Even with a homogeneous illumination light beam, the detected intensity of the illumination system may not be accurate due to noise of the captured images of the micromirrors in the photodetector.

An approach to solve this problem is to calibrate the illumination intensity of the light source as disclosed in the invention. Moreover, the solution may include a solution to depress the noise in the captured images generated by the photodetector. According to an embodiment of the invention, an image of the micromirrors is taken by the photodetector when the light source is turned off. The illumination intensity of the background noise in captured image is analyzed and recorded. The micromirror array device under inspection is then replaced by a reference wafer, such as a glass plate preferably having a reflective index higher than that of the micromirror array device. A reference illumination intensity is then measured for the reference wafer with the light source turned on. The noise intensity and the reference intensity are respectively defined as the minimum and maximum illumination intensities allowed by the photodetector. The measured illumination intensity of the reflected light in a practical measurement is then scaled within the dynamic intensity range between the minimum and maximum illumination intensities.

Figure 12:
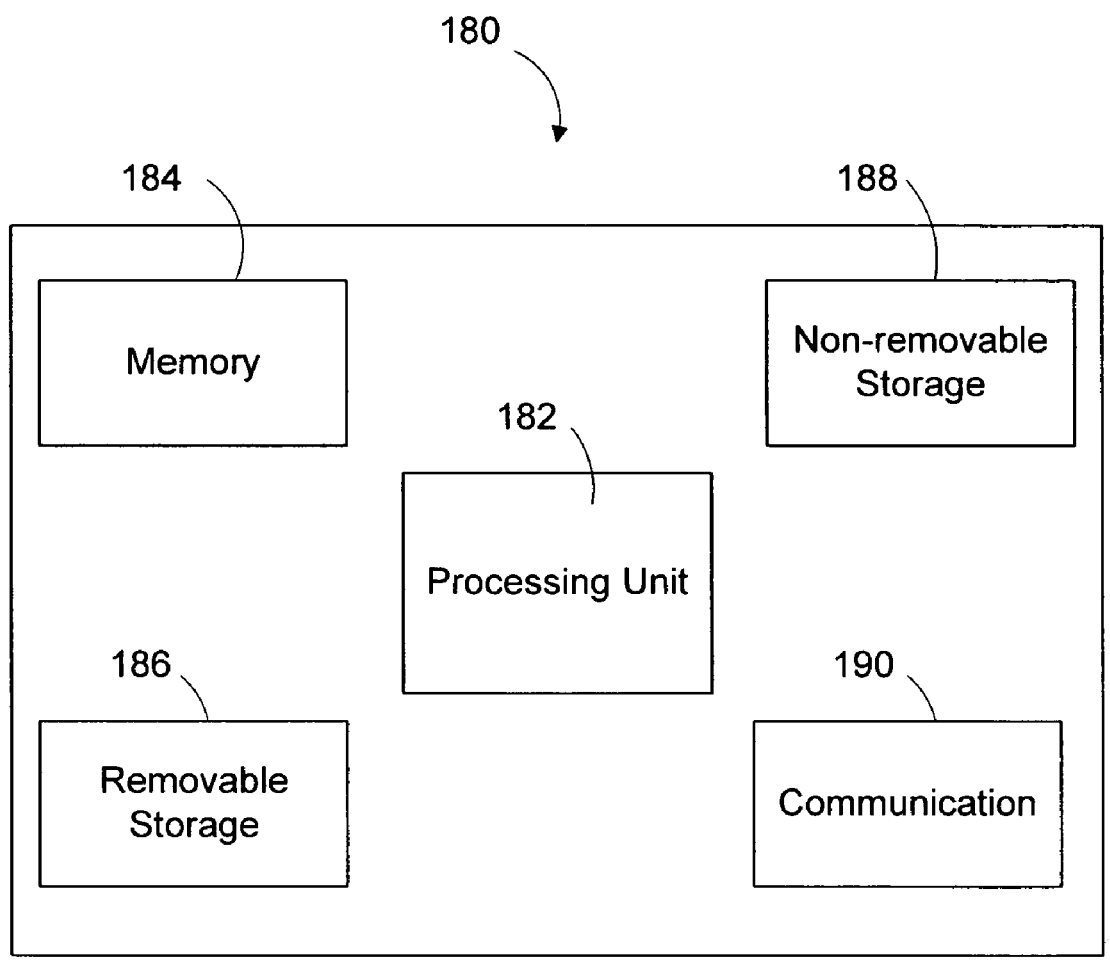
FIG. 12 schematically illustrates a simplified computing system for use in performing the methods of the invention.

According to an embodiment of the invention, measurement procedures as discussed above can be implemented in a computing device, such as computing device 154 in FIG. 5. Specifically, the computing device controls the components of the measurement system based on the interaction with users, or based on the control information stored therein so as to perform the measurement procedure. The control can be accomplished through executions of a plurality of computer readable instructions generated from a plurality of functional modules. FIG. 12 schematically illustrates one exemplary computing device for implementing embodiments of the invention. Although such devices are well known to those of skill in the art, a brief explanation will be provided herein for the convenience of other readers.

Referring to FIG. 12, in its most basic configuration, computing device 180 typically includes at least one processing unit 182 and memory 184. Depending on the exact configuration and type of computing device, memory 184 can be volatile (such as RAM), non-volatile (such as ROM, flash memory, etc.) or some combination of the two.

Additionally, device 180 may also have other features and/or functionality. For example, device 180 could also include additional removable and/or non-removable storage including, but not limited to, magnetic or optical disks or tape, as well as writable electrical storage media. Such additional storage is illustrated in FIG. 12 by removable storage 186 and non-removable storage 188. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology, CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 190 that allow the device to communicate with other devices (such as the other functional modules in FIG. 5). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. As discussed above, the term computer readable media as used herein includes both storage media and communication media.

Figure 13:
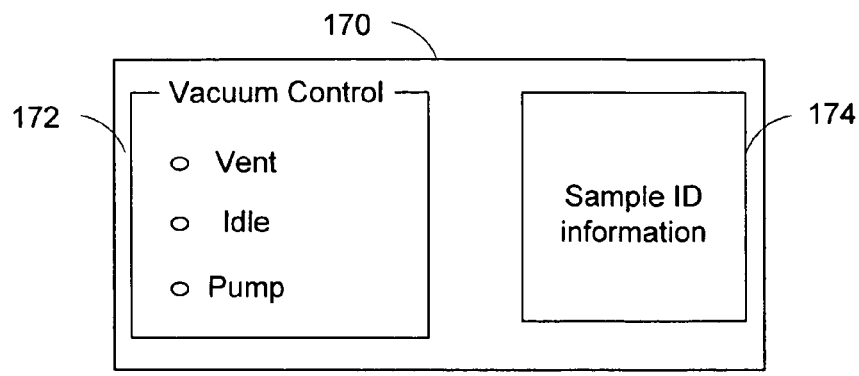
FIG. 13 demonstratively illustrates an user-interface used for controlling the vacuum of the experimental setup.

For facilitating the automatic control of the measurements system for executing the desired measurement procedures with the computing device, a set of User-Interfaces (UI) are provided according to the invention. FIG. 13 illustrates UI 170 through which parameters associated with the sample loading (e.g. step 156 shown in FIG. 6) can be defined. Specifically, UI 170 provides vacuum control panel 172 for enabling the user to control the vacuum of the system. For example, the user may activate "Vent" for ventilating vacuum chamber 150 in FIG. 5. This is often executed after each measurement and/or before loading one or more new sample into the vacuum chamber. The user may activate "Idle" for maintaining the vacuum system at its current state. When the sample (e.g. spatial light modulators) are securely loaded into the vacuum chamber of the system, the user may instruct the system to pumping out the vacuum chamber to a desired pressure level, such 1 atmosphere or lower, or 20 Torr or less, or 50 mTorr or less, or 15 mTorr or less. This can be accomplished by activating "Pump." When the system reaches the desired measurement environment (e.g. the desire pressure), the user may instruct the system to maintain its current state by activating "Idle." The desired measurement can then be performed. After the completion of the measurements, the user may instruct the measurement system to ventilating the vacuum chamber so as to unload the sample. The ventilation of the vacuum system can be done with the activation of "Vent."

Before (or after) performing the measurement, information for uniquely identifying the sample to be measured can be recorded in panel 174 as shown in the figure. This information will be associated with the measurements results of the sample and can be stored in the computing device or other type of storages.

In performing measurement, the rotational positions of the mirror plates of the micromirrors are detected through the measurements of the illumination intensities of the corresponding image cells. To accomplish this, the image cells, especially the centers of the image cells are required to be aligned to the physical centers of the mirror plates when the mirror plates are at their natural resting states, such as parallel to the substrate. Accordingly, an alignment control mechanism is necessary. For this reason, align control UI 176 is provided and an exemplary of which is presented in FIG. 14.

Figure 14:
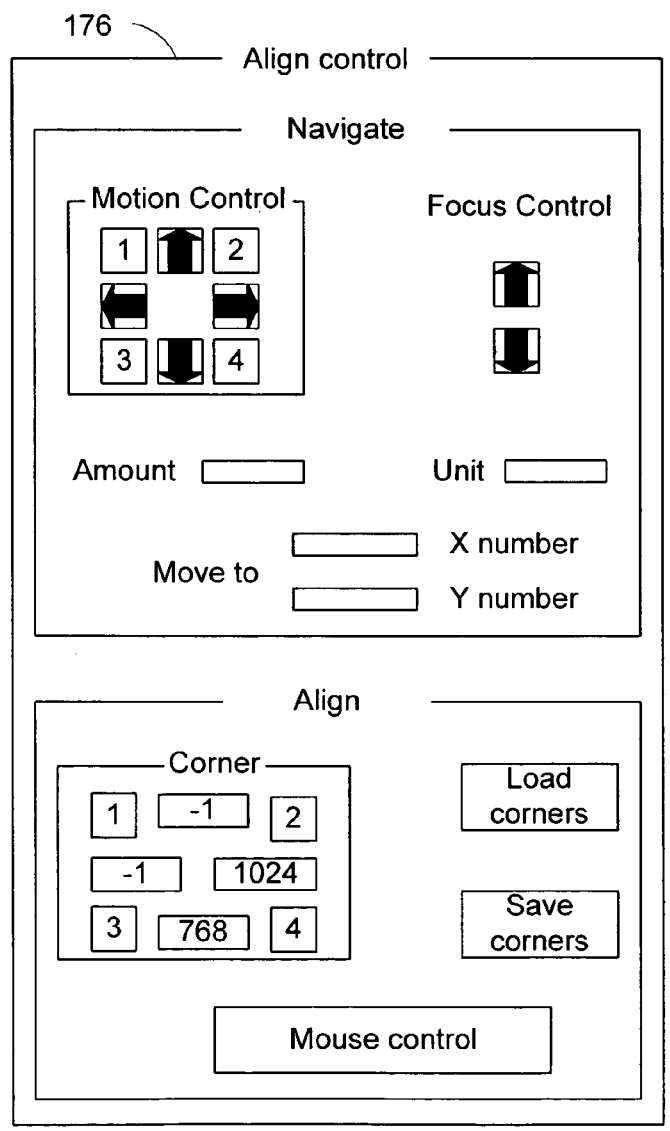
FIG. 14 demonstratively illustrates an user-interface used for aligning the micromirrors of the micromirror array device to the experimental setup.

Referring to FIG. 14, align control UI 176 consists of a navigate control panel and an align control panels. The navigate control panel further comprises motional control panel, in which motion direction keys are provided. Through the motion direction keys, the sample (e.g. the spatial light modulator in the vacuum chamber) and/or the illumination system (e.g. 144 in FIG. 5) can be relatively moved in "left", "right", "up" and "down" directions so as to accomplish the alignment. The movement can control through other control fields provided by the navigate panel. For example, the "Amount" field, which consists of a text-input field allows for the user to indicate the movement increment with a unit defined in the "Unit" field that also comprises a text-input field. In addition to step-movement, the navigate panel further provides a "Move to" function for enabling the alignment of the illumination system with any micromirror in the inspection field. Specifically, the "Move to" field consists of a field of "X number" in which the X coordinate (in terms of the number of micromirrors) of the mirror plate to be aligned is indicted, and a field of "Y number" in which the Y coordinate (in terms of the number of micromirrors) of the mirror plate to be aligned is indicted. In addition to the position control, the navigate control panel also provides the function for controlling the optical elements of the measurements system so as to obtain the best quality image of the micromirrors. Specifically, a "Focus Control" is provided for controlling the optical elements, such as projection lens 144, 146, 148, and 152.

When the micromirrors of spatial light modulator being tested are aligned with the illumination system, the inspection region, as well as thither position information needs to be defined. Accordingly, the align control panel provides an "Align" panel as shown in the figure. The "Align" panel consists of a "Corner" panel in which the coordinates of the micromirrors at the four (4) corners of the spatial light modulator are defined. As an example of a spatial light modulator having 1024×768 micromirrors, the coordinates of the micromirror at the top-left corner of the spatial light modulator can be set as (−1, −1). The coordinates of the micromirror at the top-right corner can be set as (1024, −1). The coordinates of the micromirror at the bottom-right corner can be set as (1024, 768), and the coordinates of the micromirror at the bottom-left corner can be set as (−1, 768). These coordinates of the corner micromirrors can be stored through activation "Save corners" in the panel. Alternatively, the coordinates of the corner micromirrors can be loaded from storage through the activation of "Load Corners." In addition to indicating the coordinates of the corner micromirrors with numbers, the "Align Control" panel also provides "Mouse Control" function enabling the user to control the alignment with a mouse of the computing device.

In performing the measurement, a voltage scanning scheme is defined, such as in step 162 of the flow chart in FIG. 6. The voltage scanning scheme can be defined through UI 178 as shown in FIG. 15. Referring to FIG. 15, UI 178 comprises "Polarity" panel, "Voltage scan test settings" panel, "Data analysis settings" panel, "Alternative scan settings" panel, and other related functional and operational buttons, such as "Start voltage scan", "save voltage scan", and "Analyze scan results" and an "Intensity threshold" text-input field, and "Alternative scan settings" panel.

The "Polarity" panel provides users with a plurality of options, such as "Positive" and "Negative" for enabling the users to indicate the polarity of the driving voltages. The driving voltages used for the measurements, such as those illustrated in FIG. 8 through 11, are further defined in the "voltage scan test settings" panel. Specifically, the voltage scan scheme can be selected from a plurality of provided options. As an example, the user may use "Sequence 1" and "Sequence 2" panels to define the voltage scan sequence as shown in FIG. 8. Specifically, the upward scanning portion can be defined in the "Sequence 1" panel. The "Voltage Min A," "Voltage Max B" and "Voltage Min C" fields respectively define the starting voltage, the maximum voltage $V_{max}$ and the ending voltage. The downwards voltage scanning portion of voltage profile can be defined with "Sequence 2" panel. The "Voltage Min D," "Voltage Max E" and "Voltage Min F" respectively define the starting voltage the downwards scanning voltage, the maximum voltage in the negative voltage direction, and the returning voltage. The slop of scanning voltage profile can be defined in the "Voltage step" field, which can be a text-input field.

The "data analysis settings" panel is provided for defining the number of micromirrors in the inspection area. For example, the measurement setup and the method according to the invention enable 20 or more, or 35×35 or more, or 128×92 or more micromirrors being included in the inspection area.

In addition to the voltage profile in FIG. 8, other voltage profiles, such that in FIG. 9 can also be defined, for example, through the "Alternative scan settings" panel. In particular, the starting voltage can be defined in the text-input filed "Min Voltage;" the voltage peak of $T_2$ can be defined in the text-input filed "Mid Voltage;" and the voltage peak of $T_1$ can be defined in the text-input filed "Max Voltage." The "Voltage step 1" defines the voltage increment step of the voltage peak of $T_2$. In fact, the "Alternative scan settings" panel can also be used to defining the voltage profile in FIG. 11 by, fro example, setting the "Min Voltage" and "Mid Voltage" fields to zero, and the "Voltage Step 1" to a desired voltage increment step. The scanning voltage having the profile defined above can be activated and applied to the micromirrors during measurements by checking the "Use Alt Voltage Scan."

Given the selected and defined voltage scan scheme and scanning voltage profile, the measurement can be initiated by activating the functional button of "Start voltage scan." After each scan for either a micromirror or the micromirrors within the defined inspection area or the micromirrors of the spatial light modulator, the scanned results can be saved through activation of the functional button of "Save voltage scan." The results can then be analyzed by activating the functional button of "Analyze scan results." In the measurement, the rotational positions of the mirror plates are detected through the measurements of the intensities of the reflected light from the mirror plates, which is measured through the captured images of the mirror plates. For better presenting such intensities in the image, an intensity threshold is determined for filtering out the intensities beyond the threshold. As a result, the centers of the mirror plates are more discernable; and the intensities around the center if the mirror plate image can be more accurately compared with each other.

In addition to selection of the scanning voltages from the predefined (or provided) options, the method and experimental setup including UI 178 according to the invention also enable the user to perform the measurements with any desired voltage scanning schemes or scanning voltage profiles. This can be accomplished through the definition of the voltage profile with UI 178, which will not be discussed in detail herein.

Figure 16A:
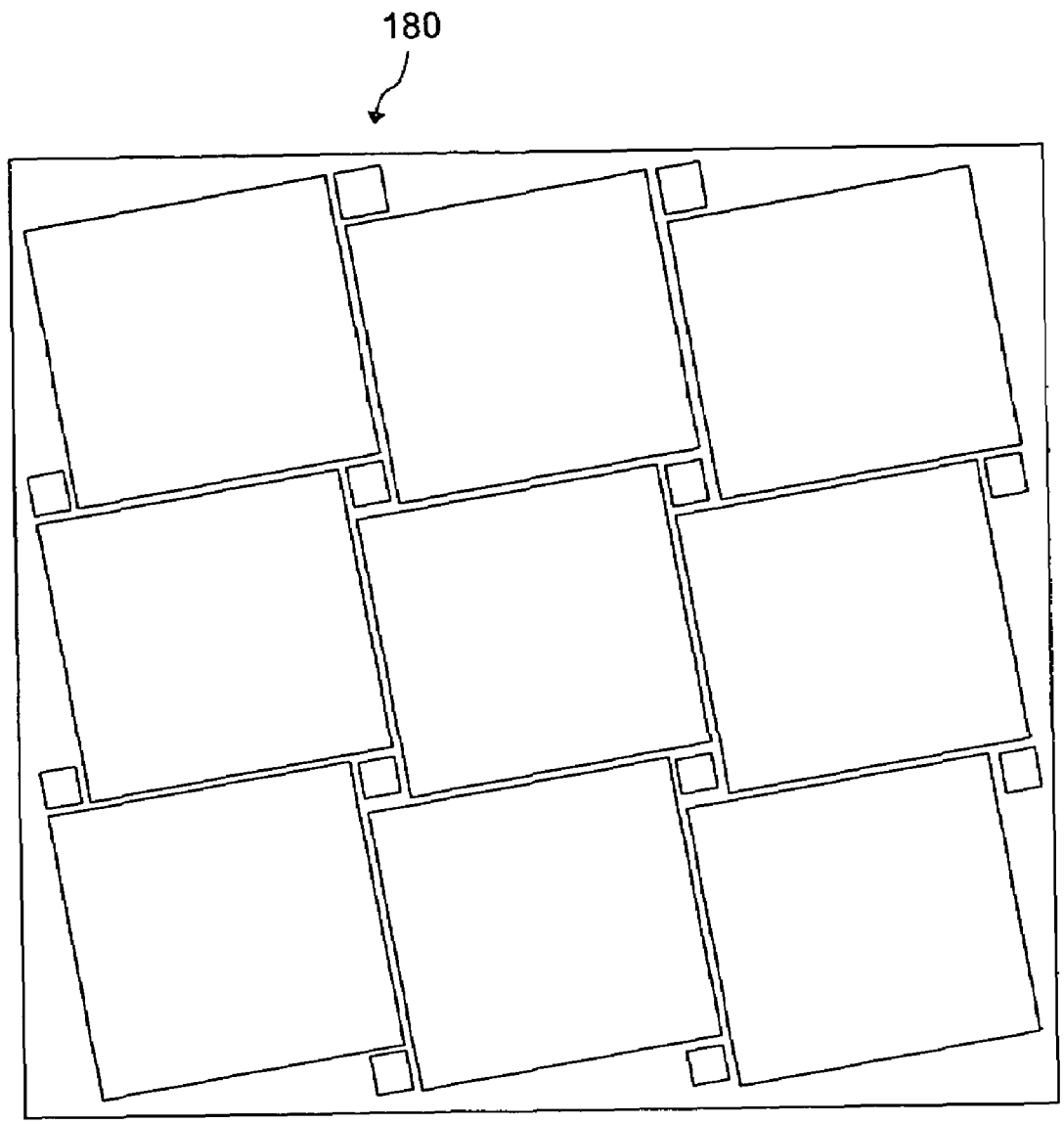
FIG. 16A is a top view of another micromirror array device in which the embodiment of the invention can be implemented.
Figure 16B:
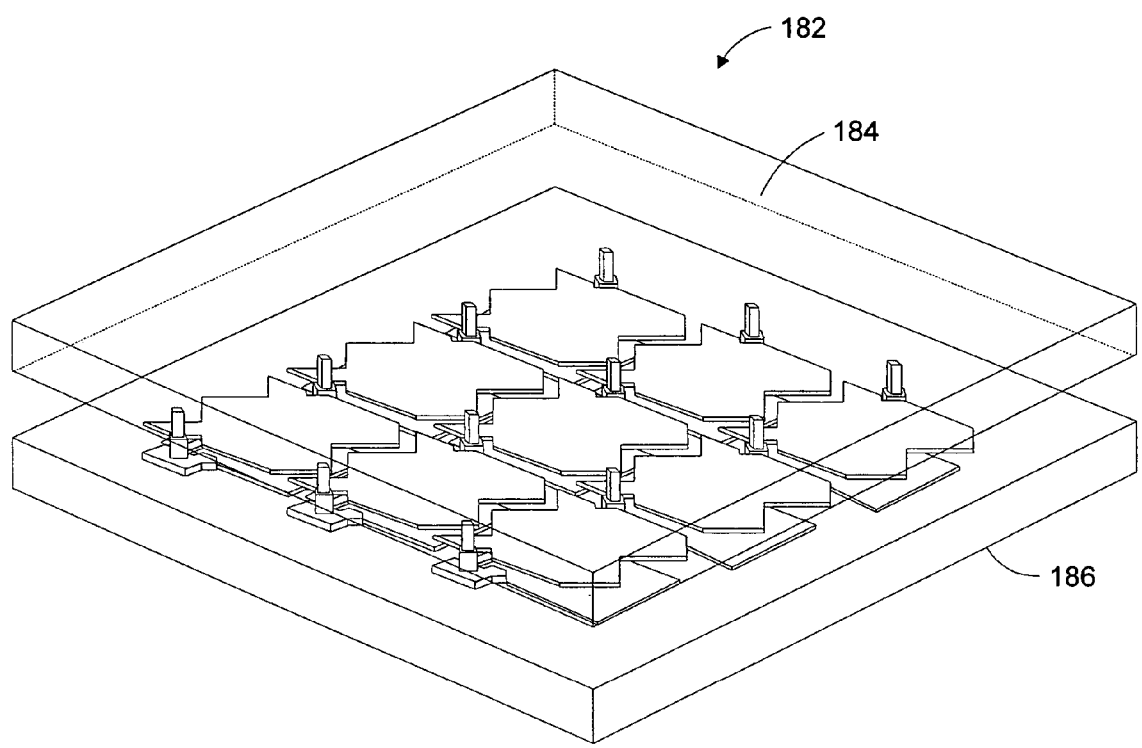
FIG. 16B is a perspective view of yet another micromirror array device in which the embodiment of the invention can be implemented.

In addition to the implementation in the micromirror devices as shown in FIG. 1, the present invention can also be implemented in measuring other type of micromirror array devices, such as those illustrated in FIGS. 16A and 16B.

Referring to FIG. 16A, the micromirrors are arranged in the micromirror array such that the micromirrors in the array are titled—that is the edges of the mirror plate of each micromirror in the array are neither parallel to the edges of the micromirror array nor parallel to the edges of the micromirror array device, as set forth in U.S. patent application Ser. No. 10/698,563 to Patel, filed on Oct. 30, 2003, the subject matter being incorporated herein by reference.

Referring to FIG. 16B, another micromirror array device in which embodiments of the invention can be implemented is illustrated therein. The mirror plates of the micromirrors in the micromirror array each have zigzagged edges. An advantage of such a mirror plate is that the unexpected light scattering can be reduced, thus, the contrast ratio of the displayed images can be improved. Similar to that in FIG. 1, the micromirrors can be formed on a light transmissive substrate 184, which can be glass. The electrode and circuitry array can be formed on semiconductor substrate 186 for addressing and actuating the micromirrors. Alternatively, the micromirrors and the electrodes can be formed on the same substrate, such as a semiconductor substrate.

It will be appreciated by those of skill in the art that a new and useful method and a system for qualitatively evaluating product quality of microelectromechanical devices have been described herein. In view of the many possible embodiments to which the principles of this invention may be applied, however, it should be recognized that the embodiments described herein with respect to the drawing figures are meant to be illustrative only and should not be taken as limiting the scope of invention. For example, the micromirror array device can be a part of a packaged device. The device package may have the micromirror array device being hermetically or non-hermetically sealed within the package. Those of skill in the art will recognize that the illustrated embodiments can be modified in arrangement and detail without departing from the spirit of the invention. Therefore, the invention as described herein contemplates all such embodiments as may come within the scope of the following claims and equivalents thereof.

APPENDIX A

A Brief Description of the Sobel Detector

The Sobel operator performs a 2-D spatial gradient measurement on an image and so emphasizes regions of high spatial gradient that correspond to edges. Typically it is used to find the approximate absolute gradient magnitude at each point in an input grey-scale image. In theory at least, the operator consists of a pair of 3×3 convolution masks as shown in the following. A brief description of the convolution operator is attached in Appendix B. One mask is simply the other rotated by 90°.

| -1 | 0 | +1 |   | +1 | +2 | +1 |
|----|---|----|---|----|----|----|
| -2 | 0 | +2 |   | 0  | 0  | 0  |
| -1 | 0 | +1 |   | -1 | -2 | -1 |

Gx             Gy

Sobel convolution masks

These masks are designed to respond maximally to edges running vertically and horizontally relative to the pixel grid, one mask for each of the two perpendicular orientations. The masks can be applied separately to the input image, to produce separate measurements of the gradient component in each orientation (call these Gx and Gy). These can then be combined together to find the absolute magnitude of the gradient at each point and the orientation of that gradient. The gradient magnitude is given by:

$$|G|=\sqrt{Gx^2+Gy^2}$$

Although typically, an approximate magnitude is computed using:

$$|G|=|Gx|+|Gy|$$

which is much faster to compute.

The angle of orientation of the edge (relative to the pixel grid) giving rise to the spatial gradient is given by:

$$\theta=\arctan(Gy/Gx)-3\pi/4$$

In this case, orientation 0 is taken to mean that the direction of maximum contrast from black to white runs from left to right on the image, and other angles are measured anti-clockwise from this. Often, this absolute magnitude is the only output the user sees—the two components of the gradient are conveniently computed and added in a single pass over the input image using the pseudo-convolution operator shown in the following figure.

| $P_1$ | $P_2$ | $P_3$ |
|-------|-------|-------|
| $P_4$ | $P_5$ | $P_6$ |
| $P_7$ | $P_8$ | $P_9$ |

Pseudo-convolution masks used to quickly compute approximate gradient magnitude

Using this mask the approximate magnitude is given by:

$$\|G\|=|(P_1+2\times P_2+P_3)-(P_7+2\times P_8+P_9)|+|(P_3+2\times P_6+P_9)-(P_1+2\times P_4+P_7)|$$

APPENDIX B

A Brief Description of Convolution

Convolution is a simple mathematical operation which is fundamental to many common image processing operators. Convolution provides a way of 'multiplying together' two arrays of numbers, generally of different sizes, but of the same dimensionality, to produce a third array of numbers of the same dimensionality. This can be used in image processing to implement operators whose output pixel values are simple linear combinations of certain input pixel values.

In an image processing context, one of the input arrays is normally just a greylevel image. The second array is usually much smaller, and is also two dimensional (although it may be just a single pixel thick). The following shows an example image and kernel that we will use to illustrate convolution.

| $I_{11}$ | $I_{12}$ | $I_{13}$ | $I_{14}$ | $I_{15}$ | $I_{16}$ | $I_{17}$ | $I_{18}$ | $I_{19}$ |
|----------|----------|----------|----------|----------|----------|----------|----------|----------|
| $I_{21}$ | $I_{22}$ | $I_{23}$ | $I_{24}$ | $I_{25}$ | $I_{26}$ | $I_{27}$ | $I_{28}$ | $I_{29}$ |
| $I_{31}$ | $I_{32}$ | $I_{33}$ | $I_{34}$ | $I_{35}$ | $I_{36}$ | $I_{37}$ | $I_{38}$ | $I_{39}$ |
| $I_{41}$ | $I_{42}$ | $I_{43}$ | $I_{44}$ | $I_{45}$ | $I_{46}$ | $I_{47}$ | $I_{48}$ | $I_{49}$ |
| $I_{51}$ | $I_{52}$ | $I_{53}$ | $I_{54}$ | $I_{55}$ | $I_{56}$ | $I_{57}$ | $I_{58}$ | $I_{59}$ |
| $I_{61}$ | $I_{62}$ | $I_{63}$ | $I_{64}$ | $I_{65}$ | $I_{66}$ | $I_{67}$ | $I_{68}$ | $I_{69}$ |

| $K_{11}$ | $K_{12}$ | $K_{13}$ |
|----------|----------|----------|
| $K_{21}$ | $K_{22}$ | $K_{23}$ |

An example small image (left) and kernel (right) for illustrating convolution. The labels within each grid square are used to identify each square.

The convolution is performed by sliding the kernel over the image, generally starting at the top left corner, so as to move the kernel through all the positions where the kernel fits entirely within the boundaries of the image. (Note that implementations differ in what they do at the edges of images as explained below.) Each kernel position corresponds to a single output pixel, the value of which is calculated by multiplying together the kernel value and the underlying image pixel value for each of the cells in the kernel, and then adding all these numbers together.

So in this example, the value of the bottom right pixel in the output image will be given by:

$$O_{57}=I_{57}K_{11}+I_{58}K_{12}+I_{59}K_{13}+I_{67}K_{21}+I_{68}K_{22}+I_{69}K_{23}$$

If the image has M rows and N columns, and the kernel has m rows and n columns, then the size of the output image will have M−m+1 rows, and N−n+1 columns. Mathematically we can write the convolution as:

$$O(i, j) = \sum_{k=1}^{m} \sum_{l=1}^{n} I(i+k-1, j+l-1) K(k, l)$$

wherein i runs from 1 to M−m+1 and j runs from 1 to N−n+1. Note that many implementations of convolution produce a larger output image than this because they relax the constraint that the kernel can only be moved to positions where it fits entirely within the image. Instead, these implementations typically slide the kernel to all positions where just the top left corner of the kernel is within the image. Therefore the kernel 'overlaps' the image on the bottom and right edges. One advantage of this approach is that the output image is the same size as the input image. Unfortunately, in order to calculate the output pixel values for the bottom and right edges of the image, it is necessary to invent input pixel values for places where the kernel extends off the end of the image. Typically pixel values of zero are chosen for regions outside the true image, but this can often distort the output image at these places. Therefore in general if you are using a convolution implementation that does this, it is better to clip the image to remove these spurious regions. Removing n−1 pixels from the right hand side and m−1 pixels from the bottom will fix things

We claim:

1. A method, of evaluating a quality of an array of micromirrors, each micromirror having a mirror plate, the method comprising:
   (a) directing a beam of electromagnetic radiation to a mirror plate of a micromirror in an array of micromirrors while altering a position of the mirror plate;
   (b) detecting a dynamic variation in an intensity of the electromagnetic radiation reflected from the mirror plate over time;
   (c) determining the quality of array of micromirrors based on the dynamic variation in the intensity of the electromagnetic radiation reflected from the mirror plate; and
   (d) determining and storing an acceptability of the array of micromirrors based on the quality of the micromirror array.

2. The method of claim 1, wherein the altering a position of the mirror plate is achieved by an application of an electrostatic field having an amplitude altering over time.

3. A method of characterizing an array of micromirrors, each micromirror having a reflective deflectable mirror plate, the method comprising:
   directing a beam of electromagnetic radiation to the array of micromirrors;
   applying a voltage so as to sequentially move individual reflective deflectable mirror plates in the array of micromirrors, while observing an intensity of the electromagnetic radiation reflected from the individual reflective deflectable mirror plates
   detecting the intensity vs. the voltage as the individual reflective deflectable mirror plates move;
   determining a characteristic of at least one of the individual reflective deflectable mirror plates based upon the intensity vs. voltage; and
   determining and storing whether the array of micromirrors is acceptable based upon the characteristic of the at least one of the individual reflective deflectable mirror plates.

4. The method of claim 3, wherein the at least one of the individual reflective deflectable mirror plates moves to an ON state angle.

5. The method of claim 4, wherein the characteristic is a time interval during which the at least one of the individual reflective deflectable mirror plates is rotated to the ON state angle from an OFF state angle.

6. The method of claim 3, wherein the characteristic is an ON state voltage under which the at least one of the individual reflective deflectable mirror plates is at an ON state angle.

7. The method of claim 3, wherein the at least one of the reflective deflectable mirror plates moves to an OFF state angle.

8. The method of claim 7, wherein the characteristic is an OFF state voltage under which the at least one of the individual reflective deflectable mirror plates is at the OFF state angle.

9. The method of claim 7, wherein the characteristic is a time interval during which the at least one of the reflective deflectable mirror plates is rotated to the OFF state angle from an ON state angle.

10. The method of claim 3, wherein the characteristic includes an ON state voltage under which the at least one of the reflective deflectable mirror plates is at an ON state, and a time interval during which the at least one of the reflective deflectable mirror plates is rotated to the ON state from an OFF state.

11. The method of claim 3, wherein the characteristic includes an OFF state voltage under which the at least one of the reflective deflectable mirror plates is at an OFF state, and a time interval during which the at least one of the reflective deflectable mirror plates is rotated to the OFF state from an ON state.

* * * * *